United States Patent
Moshe

(10) Patent No.: US 7,307,729 B2
(45) Date of Patent: Dec. 11, 2007

(54) ELECTRO-OPTICALLY INSPECTING AND DETERMINING INTERNAL PROPERTIES AND CHARACTERISTICS OF A LONGITUDINALLY MOVING ROD OF MATERIAL

(75) Inventor: Danny S. Moshe, Kiryat Ono (IL)

(73) Assignee: Green Vision Systems Ltd., Tel-Aviv (IL)

( * ) Notice: Subject to any disclaimer, the term of this patent is extended or adjusted under 35 U.S.C. 154(b) by 184 days.

(21) Appl. No.: 10/525,051

(22) PCT Filed: Aug. 19, 2003

(86) PCT No.: PCT/IL03/00688

§ 371 (c)(1),
(2), (4) Date: Feb. 18, 2005

(87) PCT Pub. No.: WO2004/017099

PCT Pub. Date: Feb. 26, 2004

(65) Prior Publication Data

US 2006/0033919 A1   Feb. 16, 2006

Related U.S. Application Data

(60) Provisional application No. 60/404,144, filed on Aug. 19, 2002.

(51) Int. Cl.
*G01N 21/84* (2006.01)

(52) U.S. Cl. .................................. 356/430; 356/431

(58) Field of Classification Search ................ 356/429, 356/430, 431; 131/84.1
See application file for complete search history.

(56) References Cited

U.S. PATENT DOCUMENTS 3,980,567 A   9/1976 Benini
4,090,794 A   5/1978 Benini
RE29,839 E   11/1978 McLoughlin et al.
4,208,578 A   6/1980 McLoughlin et al.
4,377,743 A   3/1983 Bolt et al.
4,563,095 A *  1/1986 Puffer ........................ 356/430
4,606,634 A   8/1986 Bieringer
4,610,542 A   9/1986 Ringlien
4,639,592 A   1/1987 Heitmann
4,645,921 A   2/1987 Heitmann et al.
5,013,905 A   5/1991 Neri
5,041,736 A *  8/1991 Kyriakis ................. 250/559.12

(Continued)

FOREIGN PATENT DOCUMENTS

WO   WO 2004/017099   2/2004

*Primary Examiner*—Roy M. Punnoose

(57) ABSTRACT

Electro-optically inspecting a longitudinally moving rod of material (12). Guiding rod (12) along its longitudinal axis by rod guiding unit (14), along optical path (20) within transparent passageway (22). Optical path (20) and transparent passageway (22) coaxially extend along longitudinal axis of rod (12) and pass through an electro-optical transmission module (24). Focused beam (28) from illumination unit (26) is transmitted through first side (30) of transparent passageway (22) and incident upon rod (12) within transparent passageway (22). Illuminating volumetric segment (34) of rod (12) by incident beam (32), such that incident beam (32) is affected by and transmitted through volumetric segment (34) and transmitted through second side (36) of transparent passageway (22), for forming rod material transmitted beam (38). Detecting transmitted beam (38) by detection unit (40), for forming rod material volumetric segment transmitted beam useable for determining internal properties and characteristics of rod of material (12).

73 Claims, 2 Drawing Sheets

U.S. PATENT DOCUMENTS

| | | |
|---|---|---|
| 5,228,462 A | 7/1993 | Osmalov et al. |
| 5,353,356 A | 10/1994 | Waugh et al. |
| 5,371,584 A * | 12/1994 | Scheinhutte ............. 356/238.3 |
| 5,432,600 A | 7/1995 | Grollimund et al. |
| 5,448,365 A | 9/1995 | Grollimund et al. |
| 6,020,969 A | 2/2000 | Struckhoff et al. |
| 6,213,128 B1 * | 4/2001 | Smith et al. ................ 131/280 |
| 6,301,380 B1 | 10/2001 | Mullins et al. |
| 2001/0001390 A1 | 5/2001 | Smith et al. |

* cited by examiner

_US 7,307,729 B2_

ELECTRO-OPTICALLY INSPECTING AND DETERMINING INTERNAL PROPERTIES AND CHARACTERISTICS OF A LONGITUDINALLY MOVING ROD OF MATERIAL

RELATED PATENT APPLICATION

This application is a National Phase Application of PCT/IL03/00688 having International Filing Date of 19 Aug. 2003, which claims priority from U.S. Provisional Patent Application No. 60/404,144 filed 19 Aug. 2002.

FIELD AND BACKGROUND OF THE INVENTION

The present invention relates to using electro-optics for inspecting and determining internal properties and characteristics of a longitudinally moving rod of material, and more particularly, to a method and device for electro-optically inspecting and determining internal properties and characteristics, such as density, structure, defects, and impurities, and variabilities thereof, of a longitudinally moving rod of material. The rod of material is continuously or intermittently moving along its longitudinal axis while at least one focused beam of electromagnetic radiation is incident upon, measurably affected by, and transmitted through, volumetric segments of the longitudinally moving rod of material, along with detecting the transmitted electromagnetic radiation beam, during the electro-optical inspection process of measuring and analyzing the internal properties and characteristics of the longitudinally moving rod of material. The present invention is generally applicable for inspecting and determining internal properties and characteristics of a variety of different types of a rod of material, as long as the rod of material exhibits the behavior that an incident focused beam of electromagnetic radiation, while not altering the rod of material, is affected by and transmittable through volumetric segments of the rod of material. For example, but not limited to, a cigarette rod consisting of processed tobacco inside a rolled and sealed tube of cigarette wrapping paper.

The present invention is particularly applicable to that stage of an overall commercial manufacturing sequence involving continuously transporting or conveying a rod of material between manufacturing processes. There exist overall commercial manufacturing sequences including a stage whereby raw or initially processed material exiting an upstream manufacturing process is formed into a short discrete or long continuous rod of material, which is either wrapped inside a wrapping material or is left unwrapped, and continuously transported or conveyed prior to entering further downstream processes, including for example, a rod cutting process, eventually leading to production of bulk quantities of individually wrapped or unwrapped consumer product. For example, in the case of manufacturing cigarettes, as part of an overall commercial manufacturing sequence, bulk quantities of cut and processed tobacco leaves, along with any number of cigarette tobacco additives or ingredients, exiting an upstream manufacturing process are rolled, wrapped, and sealed, inside cigarette wrapping paper, and continuously transported or conveyed as long, narrow, continuous tobacco filled cylinders or rods prior to entering further downstream processes, including for example, a cigarette rod cutting process, eventually leading to production of bulk quantities of individually cut, wrapped, and non-filtered or filtered, cigarettes in a box.

During such a manufacturing sequence, internal properties and characteristics, such as density, structure, defects, impurities, and variabilities thereof, of the continuously moving rod of material exiting an upstream manufacturing process, may feature values outside of acceptable ranges and/or may undesirably change prior to entering a downstream manufacturing process. At this stage of such a manufacturing sequence, it is critically important that these internal properties and characteristics of the continuously moving rod of material be determined and monitored, such as by employing quality control and quality assurance procedures, and subsequently controlled, such as by employing process control and process feedback procedures, prior to the continuously moving rod of material entering further downstream processes or storage, in order to assure proper characteristics and performance of the finished end products.

In particular, if one or more of the above indicated internal properties and characteristics of a given portion or section of the continuously moving rod of material is outside of established quality control or quality assurance values, use of such portion or section of the rod of material is expected to lead to downstream intermediate products, or stored rod of material, similarly failing their established quality control values, potentially causing undesirable rejection of material, manufacturing down time and added cost to the overall manufacturing sequence. For example, in the case of manufacturing cigarettes, if one or more of the above indicated internal properties and characteristics of a given portion or section of the rod shaped wrapped cigarette tobacco are outside of established quality control values, at least that portion or section of the tobacco filled rod needs to be removed prior to entering further downstream processes or storage, otherwise, 'below quality' cigarettes may end up in the consumer marketplace, clearly undesirable to a cigarette manufacturer, as well as undesirable to consumers of cigarettes.

Herein, internal properties and characteristics, such as density, structure, defects, and impurities, and variabilities thereof, of a longitudinally moving rod of material refer to the global, bulk, or macroscopic, internal properties and characteristics, such as density, structure, defects, and impurities, and variabilities thereof, of a specified volumetric segment or number of volumetric segments of the material, including bulk or macroscopic volume occupied by air and moisture throughout the material, making up or forming the longitudinally moving rod of material. These internal properties and characteristics of the longitudinally moving rod are to be clearly distinguished from the local, molecular, or microscopic, properties and characteristics, such as molecular density, molecular structure, microscopic defects, and microscopic impurities, and variabilities thereof, of only the material, excluding bulk or macroscopic volume occupied by air and moisture, making up or forming the longitudinally moving rod of material.

For example, internal properties and characteristics, such as density, structure, defects, and impurities, and variabilities thereof, of a longitudinally moving cigarette rod consisting of processed tobacco inside a rolled and sealed tube of cigarette wrapping paper, refer to the global, bulk, or macroscopic, density, structure, defects, and impurities, and variabilities thereof, of a specified volumetric segment or number of volumetric segments of the processed tobacco, including bulk or macroscopic volume occupied by air and moisture throughout the processed tobacco, inside the rolled and sealed tube of cigarette wrapping paper. These internal properties and characteristics of the longitudinally moving cigarette rod are to be clearly distinguished from the molecular density, molecular structure, microscopic defects, and microscopic impurities, and variabilities thereof, of only the processed tobacco molecules, excluding bulk or macroscopic volume occupied by air and moisture, making up or forming the longitudinally moving cigarette rod.

There is an extensive amount of prior art teachings of methods, devices, and systems, for electro-optically inspecting and determining 'external' (and not 'internal') properties and characteristics, such as uniformity, structure, color, print, closures, openings, defects (for example, holes, defective and/or missing components), and impurities, and variabilities thereof, of or on the 'outer or exposed surfaces' (and not of or in a specified 'volumetric segment' or number of 'volumetric segments') of a plurality of continuously or intermittently moving rods of material, where the rods of material are continuously or intermittently moving sideways along or rolling around their 'radial' axes (and not moving along their 'longitudinal' axes) during the actual electro-optical inspection process, as part of a commercial production or manufacturing sequence.

The majority of such prior art is especially with regard to electro-optically inspecting and determining properties and characteristics, such as uniformity, structure, color, print, closures, openings, defects (for example, holes, defective and/or missing components, such as a defective or missing filter), and impurities, of the outer or exposed surface, for example, of the wrapping paper, of the open end, and/or of the filter end, (and not of a specified volumetric segment or number of volumetric segments) of continuously or intermittently moving individually cut and complete cigarettes in their final form prior to packaging, moving sideways along or rolling around their radial axes. Such prior art is based on generating, detecting (collecting and measuring), and analyzing, light 'reflected by' (and not transmitted through) the outer or exposed surfaces of the continuously or intermittently moving rods of material. Such prior art may be divided into two main categories, according to the type of optics, electronics, and/or electro-optics, employed during the electro-optical inspection.

In the first main category, electro-optical inspecting is performed by generating, detecting (collecting and measuring), and analyzing, light reflected by the outer or exposed surface of at least a part of each rod of material, in the form of light beams or rays and intensities thereof. Selected examples of this main category of prior art, especially as applied to electro-optically inspecting the outer or exposed surface of at least a part of individual completed cigarettes, are the disclosures of U.S. Pat. No. 3,980,567 to Benini; U.S. Pat. No. 4,090,794 to Benini; and U.S. Pat. No. 4,639,592 to Heitmann.

In the second main category, electro-optical inspecting is performed by generating, detecting (collecting and measuring), and analyzing, light reflected by the outer or exposed surface of at least a part of each rod of material, in the form of photographic or video camera images. Selected examples of this main category of prior art, especially as applied to electro-optically inspecting the outer or exposed surface of at least a part of individual completed cigarettes, are the disclosures of U.S. Pat. No. 5,013,905 to Neri; U.S. Pat. No. 5,228,462 to Osmalov et al.; U.S. Pat. No. 5,432,600 to Grollimund et al.; and U.S. Pat. No. 5,448,365 to Grollimund et al.

The present invention is directed to commercial applications requiring real time, non-invasive, high speed, high sensitivity, low noise, high accuracy, high precision, temperature compensative, and low vibration, measuring and analyzing internal properties and characteristics, such as density, structure, defects, and impurities, and variabilities thereof, of a specified volumetric segment or number of volumetric segments, of a rod of material, such as a cigarette rod, continuously or intermittently moving along its longitudinal axis, as the rod of material is transported or conveyed during a commercial manufacturing sequence, particularly a manufacturing sequence including quality control and/or quality assurance processes.

Accordingly, each of the above cited prior art, and similar prior art, feature at least two significant and fundamental differences, and associated limitations thereof, with regard to the intended scope and applications of the present invention.

The first significant and fundamental difference is that such prior art teaches about electro-optically inspecting and determining only 'external' properties and characteristics, such as uniformity, structure, color, print, closure, defects, and impurities, and variabilities thereof, of the outer or exposed surfaces of a plurality of continuously or intermittently moving rods of material. Accordingly, such prior art teachings are solely based on generating, detecting (collecting and measuring), and analyzing, light 'reflected by', and not 'transmitted through', the outer or exposed surfaces of the continuously or intermittently moving rods of material. Such prior art teachings are not obviously extendable and/or applicable for generating, detecting (collecting and measuring), and analyzing, light transmitted through the outer or exposed surfaces of the moving rods of material, and therefore, are not obviously extendable and/or applicable for electro-optically measuring and analyzing 'internal' properties and characteristics, such as density, structure, defects, and impurities, and variabilities thereof, of a specified volumetric segment or number of volumetric segments of the material making up or forming a longitudinally moving rod of material, according to the intended scope and applications of the present invention.

The second significant and fundamental difference is that such prior art teaches about electro-optically inspecting and determining the external properties and characteristics of the outer or exposed surfaces of continuously or intermittently moving rods of material, where the rods of material are specifically restricted to moving sideways along or rolling around their 'radial' axes, and not moving along their 'longitudinal' axes, during the actual electro-optical inspection, as the rods of material are transported or conveyed during a manufacturing process. Therein is no teaching about performing the electro-optical inspection while the rods of material are moving along their longitudinal axes, during the real time electro-optical inspection, as the rods of material are transported or conveyed during a manufacturing sequence. There are commercial manufacturing sequences which either require, or where it would be highly desirable and advantageous, having a rod of material moving along its longitudinal axis, as the rod of material is transported or conveyed during the manufacturing sequence.

There are prior art teachings about electro-optically inspecting a longitudinally moving rod of material, as the rod of material is transported or conveyed during a commercial manufacturing sequence. Such prior art, particularly applicable to the cigarette manufacturing industry, selections of which are briefly described herein below, is also fundamentally different from, and features significant limitations with respect to, the intended scope and applications of the present invention.

In the disclosures of U.S. Pat. No. 6,213,128 B1, and U.S. Patent Application No. 2001/0001390 A1, both to Smith et al., there are described a method and apparatus for making and electro-optically inspecting a multi-component cigarette. As for the above previously cited prior art, the electro-optical inspection is based on generating, detecting (collecting and measuring), and analyzing, light 'reflected by', and not 'transmitted through', the outer or exposed surfaces of a variety of cigarette components, such as cigarette tobacco rods, filters, tubes, and chambers, in the form of camera images, as these cigarette components are longitudinally resting or positioned on open cigarette wrapping paper which is continuously moving along its longitudinal axis and transported or conveyed during the manufacturing sequence.

In the disclosures of U.S. Pat. No. 3,854,587; its reissue, Re. 29,839; and its improvement, U.S. Pat. No. 4,208,578, each to McLoughlin et al., there are described an "(electro-) optical inspection apparatus for monitoring a continuously (longitudinally) moving rod (in particular, a cigarette rod), comprising a circular head through which the rod passes (along its longitudinal axis), a first set of fiber optic conductors which transmits light from a source to the head to illuminate the rod, and a second set of fiber optic conductors which pick up light reflected from (and not transmitted through) the rod passing through the head and transmits the reflected light to a number of photoelectric elements. The second set of conductors are divided into angularly spaced groups around the head and adjacent groups lead to separate photoelectric elements". Outputs of the photoelectric elements are processed and analyzed by logic circuitry for determining the presence of a fault in the inspected rod, and if found, causes a fault signal to actuate a rejection mechanism when the part of the rod at which the fault has been sensed reaches a rejection point.

In the disclosure of U.S. Pat. No. 4,377,743 to Bolt et al., there is described a device and corresponding method for electro-optically inspecting a longitudinally moving rod (in particular, a cigarette rod), wherein the device comprises "a plurality of focused light emitter-detector units spaced circumferentially around a rod being inspected, each unit being arranged to propagate focused light onto a defined surface region of the rod and to receive the light reflected from (and not transmitted by) that surface region and further arranged to generate an electrical signal related to the intensity of the received light. Two, or more, axially displaced arrays of units are each arranged to inspect areas of the rod which are staggered in relation to the areas inspected by the other array or arrays".

In the Bolt et al. invention, "the measuring head of the apparatus comprises a plurality of infra-red sensor units, which each contain a light emitting diode and a phototransistor, positioned behind respective lenses. The lens for the light emitting diode focuses light onto a specific area of the cigarette rod and the lens for the phototransistor collects the light reflected from that area, i.e., "focuses" the reflected light onto the phototransistor". Outputs of the phototransistors are processed and analyzed for determining the presence of a fault in the inspected cigarette rod, and if found, causes a fault signal to actuate a cigarette ejection mechanism. The invention includes "means (a transparent tube) for guiding the continuous cigarette rod (along its longitudinal axis) along a predetermined path extending through an (electro-optical) inspection station".

In the disclosure of U.S. Pat. No. 4,645,921 to Heitmann et al., there is described an "Apparatus for optically scanning a (longitudinally) moving cigarette rod (a plurality of discrete, coaxial complete cigarettes, long continuous cigarette rods, filter rod sections, and the like) for the presence of defects in its external surface (and not internal volume) which has two annularly arranged groups of diodes which emit green light in the wavelength range of between 0.49 and 0.58.mu. and direct such light from the opposite sides of a plane that is normal to the (longitudinally) moving rod so that the incident light is reflected (and not transmitted) by successive annular portions of the external surface of the rod into the aforementioned plane. The reflected light is focused by systems of lenses upon discrete photosensitive transducers through discrete slit diaphragms on the transducers themselves or on a thin metallic ring which is adjustably mounted on the support for the diodes and the systems of lenses". The disclosed invention is "especially for scanning the circumferentially complete annular external surfaces of a series of coaxial cigarettes".

Although the prior art disclosures of Smith et al., McLoughlin et al., Bolt et al., and Heitmann et al., teach about electro-optically inspecting a longitudinally moving rod of material, such prior art teachings are solely based on generating, detecting (collecting and measuring), and analyzing, light 'reflected by' the outer or exposed surfaces of the moving rods of material, and are not obviously extendable and/or applicable for generating, detecting (collecting and measuring), and analyzing, light 'transmitted through' the outer or exposed surfaces of the moving rods of material. Accordingly, such prior art teachings are not obviously extendable and/or applicable for electro-optically measuring and analyzing 'internal' properties and characteristics, such as density, structure, defects, and impurities, and variabilities thereof, of a specified volumetric segment or number of volumetric segments of the material making up or forming a longitudinally moving rod of material, according to the intended scope and applications of the present invention.

In addition to the above described fundamental difference, a significant limitation existing in the prior art of electro-optically inspecting a longitudinally moving rod of material, regards the undesirable affect that temperature changes may have on accuracy and precision of the results obtained from the electro-optical inspection process. While electro-optically inspecting a longitudinally moving rod of material, temperature changes typically occur in critical regions of operation of the electro-optical inspection apparatus. Such critical regions of operation are particularly in the immediate vicinity of the electro-optically inspected section of the moving rod of material. Magnitudes of such temperature changes may be sufficiently large so as to significantly increase noise and error levels during the illumination and detection processes, which may translate to meaningful decreases in accuracy and precision of the results obtained from the electro-optical inspection process.

The prior art disclosures of Smith et al., McLoughlin et al., Bolt et al., and Heitmann et al., include no explicit or suggestive teaching of a procedure or of equipment for monitoring, and/or compensating for, temperature changes, in the critical region of operation of the electro-optical inspection apparatus.

Another significant limitation existing in the prior art of electro-optically inspecting a longitudinally moving rod of material, regards the undesirable affect that radially directed vibrating of the longitudinally moving rod of material, in general, and of the electro-optically inspected section of the longitudinally moving rod of material, in particular, during the electro-optical inspection process, may have on accuracy and precision of the results obtained from the electro-optical inspection process. While electro-optically inspecting a longitudinally moving rod of material, the longitudinally moving rod of material, in general, and the electro-optically inspected section of the longitudinally moving rod of material, in particular, typically vibrates, particularly, in the radial direction. Magnitudes of such radially directed vibrating may be sufficiently large so as to significantly increase noise and error levels during the illumination and detection processes, which may translate to meaningful decreases in accuracy and precision of the results obtained from the electro-optical inspection process.

The prior art disclosures of Smith et al., McLoughlin et al., Bolt et al., and Heitmann et al., include no explicit or suggestive teaching of a procedure or of equipment for preventing, eliminating, or reducing, radially directed vibrating of the longitudinally moving rod of material, in general, and of the electro-optically inspected section of the longitudinally moving rod of material, in particular, during the electro-optical inspection process.

In general, procedures and equipment for monitoring temperature and/or compensating operation of a process for temperature changes, as well as procedures and/or equipment for preventing, eliminating, or reducing, radially directed vibrating of a longitudinally moving object during operation of a process, are known and widely applicable, including on a commercial or manufacturing scale, and are well taught about. A possible reason for absence of such teachings specifically in the prior art of electro-optically inspecting a longitudinally moving rod of material, for example, as taught about in the disclosures of Smith et al., McLoughlin et al., Bolt et al., and Heitmann et al., is that the disclosed electro-optical inspection methods and apparatuses, solely based on generating, detecting (collecting and measuring), and analyzing, light reflected by the outer or exposed surfaces of the longitudinally moving rods of material, are insufficiently sensitive to be significantly affected by the above described types of local temperature changes and/or radially directed vibrating. This, therefore, precludes a need for monitoring temperature and/or compensating for such local temperature changes, or, for preventing, eliminating, or reducing, such radially directed vibrating, of the longitudinally moving rod of material during the electro-optical inspection process.

Moreover, due to physical and/or electromechanical limitations, especially regarding design, construction, and operation, of the illumination and detection units in the electro-optical inspection apparatuses taught about in McLoughlin et al., Bolt et al., and Heitmann et al., involving a plurality of miniaturized electro-optical components (in particular, light generating, conducting, emitting, and receiving, types of devices, mechanisms, components, and elements, such as LEDs, lenses, phototransistors, photosensitive transducers, fiber optic conductors or guides, and photoelectric elements) tightly configured and oriented within limited spaces, inclusion of a temperature monitoring and/or compensation procedure and equipment, and/or inclusion of a vibrating prevention, reduction, and/or compensation, procedure and equipment, operative during the electro-optical inspection process, is not readily accomplishable.

Accordingly, each of the above cited prior art, and similar prior art, feature several significant and fundamental limitations, and associated limitations thereof, with regard to the intended scope and applications of the present invention for electro-optically inspecting and determining internal properties and characteristics of a longitudinally moving rod of material.

To one of ordinary skill in the art, there is thus a need for, and it would be highly advantageous to have a method and device for electro-optically inspecting and determining internal properties and characteristics, such as density, structure, defects, and impurities, and variabilities thereof, of a longitudinally moving rod of material. Moreover, there is a need for such an invention wherein the rod of material is continuously or intermittently moving along its longitudinal axis during the electro-optical inspection process of measuring and analyzing the internal properties and characteristics of a specified volumetric segment or number of volumetric segments of the longitudinally moving rod of material.

There is also a need for such an invention which is directed to commercial applications requiring real time, non-invasive, high speed, high sensitivity, low noise, high accuracy, high precision, temperature compensative, and low vibration, measuring and analyzing of internal properties and characteristics of a longitudinally moving rod of material, as the rod of material is transported or conveyed during a commercial manufacturing sequence, particularly a manufacturing sequence including quality control and/or quality assurance processes. There is also a need for such an invention which is generally applicable for inspecting and determining internal properties and characteristics of a variety of different types of a rod of material, for example, but not limited to, a cigarette rod.

SUMMARY OF THE INVENTION

The present invention relates to a method and device for electro-optically inspecting and determining internal properties and characteristics, such as density, structure, defects, and impurities, and variabilities thereof, of a longitudinally moving rod of material. The rod of material is continuously or intermittently moving along its longitudinal axis while at least one focused beam of electromagnetic radiation is incident upon, measurably affected by, and transmitted through, volumetric segments of the longitudinally moving rod of material, along with detecting the transmitted electromagnetic radiation beam, during the electro-optical inspection process of measuring and analyzing the internal properties and characteristics of the longitudinally moving rod of material.

The present invention is generally applicable for inspecting and determining internal properties and characteristics of a variety of different types of a rod of material, as long as the rod of material exhibits the behavior that an incident focused beam of electromagnetic radiation, while not altering the rod of material, is affected by and transmittable through volumetric segments of the rod of material. For example, but not limited to, a cigarette rod consisting of processed tobacco inside a rolled and sealed tube of cigarette wrapping paper.

The present invention is directed to commercial applications requiring real time, non-invasive, high speed, high sensitivity, low noise, high accuracy, high precision, temperature compensative, and low vibration, measuring and analyzing of internal properties and characteristics of a longitudinally moving rod of material, as the rod of material is transported or conveyed during a commercial manufacturing sequence, particularly a manufacturing sequence including quality control and/or quality assurance processes.

Thus, according to the present invention, there is provided a method for electro-optically inspecting and determining internal properties and characteristics of a longitudinally moving rod of material, including the steps of: (a) guiding the longitudinally moving rod of material along its longitudinal axis by a rod guiding unit, along an optical path within a transparent passageway, the optical path and the transparent passageway coaxially extend along the longitudinal axis of the moving rod of material and pass through an electro-optical transmission module; (b) generating a focused beam of electromagnetic radiation by an illumination unit of the electro-optical transmission module, such that the focused beam is transmitted through a first side of the transparent passageway and incident upon the rod of material longitudinally moving within the transparent passageway; (c) illuminating a volumetric segment of the longitudinally moving rod of material by the incident focused beam, such that at least part of the incident focused beam is affected by and transmitted through the volumetric segment and then transmitted through a second side of the transparent passageway, for forming a rod material volumetric segment transmitted beam; and (d) detecting the rod material volumetric segment transmitted beam by a detection unit of the electro-optical transmission module, for forming a detected rod material volumetric segment transmitted beam useable for determining the internal properties and characteristics of the longitudinally moving rod of material.

According to further features in preferred embodiments of the method of the invention described below, in step (b), generating the focused beam of electromagnetic radiation by the illumination unit further includes a procedure for monitoring temperature and compensating for temperature changes in a critical region of operation of the illumination unit.

According to further features in preferred embodiments of the method of the invention described below, a critical region of operation is in immediate vicinity of the volumetric segment of the rod of material longitudinally moving along the optical path within the transparent passageway.

According to further features in preferred embodiments of the method of the invention described below, in step (b), operation of the illumination unit including the procedure for monitoring temperature and compensating for temperature changes is based on a temperature change monitoring and compensating electro-optical feedback loop.

According to further features in preferred embodiments of the method of the invention described below, in step (d), detecting the rod material volumetric segment transmitted beam by the detection unit further includes a procedure for monitoring temperature and compensating for temperature changes in a critical region of operation of the detection unit.

According to further features in preferred embodiments of the method of the invention described below, a critical region of operation is in immediate vicinity of the volumetric segment of the rod of material longitudinally moving along the optical path within the transparent passageway.

According to further features in preferred embodiments of the method of the invention described below, in step (a), the optical path and the transparent passageway coaxially extend along the longitudinal axis of the moving rod of material and pass through a plurality of two electro-optical transmission modules, such that longitudinal and angular or circumferential positions of the two electro-optical transmission modules, relative to each other, and relative to the transparent passageway within which extends the coaxial optical path, are spatially staggered or displaced along the coaxial optical path, along which the longitudinally moving rod of material is guided by the rod guiding unit.

According to further features in preferred embodiments of the method of the invention described below, the method further comprises a procedure for preventing, eliminating, or reducing, radially directed vibrating of the longitudinally moving rod of material during electro-optically inspecting the longitudinally moving rod of material.

According to further features in preferred embodiments of the method of the invention described below, wherein following step (a) and preceding step (b), there is inserted the step of generating a continuous vortical type of flow of gas within and along the transparent passageway by a vortex generating mechanism, such that the flowing gas rotates as a vortex around the optical path and around the longitudinally moving rod of material, and flows downstream within and along the transparent passageway in same longitudinal direction of the longitudinally moving rod of material, such that the flowing gas radially impinges upon the longitudinally moving rod of material within the transparent passageway; the flowing gas radially impinging upon the longitudinally moving rod of material prevents, eliminates, or reduces, radially directed vibrating of the longitudinally moving rod of material during the electro-optically inspecting the longitudinally moving rod of material.

According to another aspect of the present invention, there is provided a method for preventing, eliminating, or reducing, radially directed vibrating of a longitudinally moving rod of material during electro-optically inspecting the longitudinally moving rod of material, comprising the steps of: (a) guiding the longitudinally moving rod of material along its longitudinal axis by a rod guiding unit, along an optical path within a transparent passageway, the optical path and the transparent passageway coaxially extend along the longitudinal axis of the longitudinally moving rod of material and pass through an electro-optical inspection apparatus used for electro-optically inspecting the longitudinally moving rod of material; and (b) generating a continuous vortical type of flow of gas within and along the transparent passageway by a vortex generating mechanism, such that the flowing gas rotates as a vortex around the optical path and around the longitudinally moving rod of material, and flows downstream within and along the transparent passageway in same longitudinal direction of the longitudinally moving rod of material, such that the flowing gas radially impinges upon the longitudinally moving rod of material within the transparent passageway; the flowing gas radially impinging upon the longitudinally moving rod of material prevents, eliminates, or reduces, radially directed vibrating of the longitudinally moving rod of material during the electro-optically inspecting the longitudinally moving rod of material.

According to another aspect of the present invention, there is provided a device for electro-optically inspecting and determining internal properties and characteristics of a longitudinally moving rod of material, comprising: (a) a rod guiding unit for guiding the longitudinally moving rod of material along its longitudinal axis, along an optical path within a transparent passageway, the optical path and the transparent passageway coaxially extend along the longitudinal axis of the moving rod of material; and (b) an electro-optical transmission module through which pass the optical path and the transparent passageway, the electro-optical transmission module includes: (i) an illumination unit for generating a focused beam of electromagnetic radiation, such that the focused beam is transmitted through a first side of the transparent passageway and incident upon the rod of material longitudinally moving within the transparent passageway, the incident focused beam illuminates a volumetric segment of the longitudinally moving rod of material, such that at least part of the incident focused beam is transmitted through the volumetric segment and through a second side of the transparent passageway, for forming a rod material volumetric segment transmitted beam; and (ii) a detection unit for detecting the rod material volumetric segment transmitted beam, for forming a detected rod material volumetric segment transmitted beam useable for determining the internal properties and characteristics of the longitudinally moving rod of material.

According to further features in preferred embodiments of the device of the invention described below, the illumination unit for the generating the focused beam of electromagnetic radiation further includes components for monitoring temperature and compensating for temperature changes in a critical region of operation of the illumination unit.

According to further features in preferred embodiments of the device of the invention described below, wherein a critical region of operation is in immediate vicinity of the volumetric segment of the rod of material longitudinally moving along the optical path within the transparent passageway.

According to further features in preferred embodiments of the device of the invention described below, operation of the illumination unit including the components for monitoring temperature and compensating for temperature changes is based on a temperature change monitoring and compensating electro-optical feedback loop.

According to further features in preferred embodiments of the method of the invention described below, the detection unit for detecting the rod material volumetric segment transmitted beam further includes a procedure for monitoring temperature and compensating for temperature changes in a critical region of operation of the detection unit.

According to further features in preferred embodiments of the device of the invention described below, a critical region of operation is in immediate vicinity of the volumetric segment of the rod of material longitudinally moving along the optical path within the transparent passageway.

According to further features in preferred embodiments of the device of the invention described below, the optical path and the transparent passageway pass through a plurality of two electro-optical transmission modules, each the electro-optical transmission module includes a illumination unit and a detection unit.

According to further features in preferred embodiments of the device of the invention described below, the optical path and the transparent passageway pass through a plurality of two electro-optical transmission modules, such that longitudinal and angular or circumferential positions of the two electro-optical transmission modules, relative to each other, and relative to the transparent passageway within which extends the coaxial optical path, are spatially staggered or displaced along the coaxial optical path, along which the longitudinally moving rod of material is guided by the rod guiding unit.

According to further features in preferred embodiments of the device of the invention described below, wherein the rod guiding unit further includes a vortex generating mechanism for generating a continuous vortical type of flow of gas within and along the transparent passageway, such that the flowing gas rotates as a vortex around the optical path and around the longitudinally moving rod of material, and flows downstream within and along the transparent passageway in same longitudinal direction of the longitudinally moving rod of material, such that the flowing gas radially impinges upon the longitudinally moving rod of material within the transparent passageway; the flowing gas impinging upon the longitudinally moving rod of material prevents, eliminates, or reduces, radially directed vibrating of the longitudinally moving rod of material, during the electro-optically inspecting the longitudinally moving rod of material.

According to another aspect of the present invention, there is provided a device for preventing, eliminating, or reducing, radially directed vibrating of a longitudinally moving rod of material during electro-optically inspecting the longitudinally moving rod of material, comprising: a rod guiding unit for guiding the longitudinally moving rod of material along its longitudinal axis, along an optical path within a transparent passageway, the optical path and the transparent passageway coaxially extend along the longitudinal axis of the longitudinally moving rod of material and pass through an electro-optical inspection apparatus used for electro-optically inspecting the longitudinally moving rod of material, the rod guiding unit includes a vortex generating mechanism for generating a continuous vortical type of flow of gas within and along the transparent passageway, such that the flowing gas rotates as a vortex around the optical path and around the longitudinally moving rod of material, and flows downstream within and along the transparent passageway in same longitudinal direction of the longitudinally moving rod of material, such that the flowing gas radially impinges upon the longitudinally moving rod of material within the transparent passageway; the flowing gas impinging upon the longitudinally moving rod of material prevents, eliminates, or reduces, radially directed vibrating of the longitudinally moving rod of material, during the electro-optically inspecting the longitudinally moving rod of material.

Implementation of the method and device for electro-optically inspecting and determining internal properties and characteristics, such as density, structure, defects, and impurities, and variabilities thereof, of a longitudinally moving rod of material, of the present invention, involves performing steps and sub-steps in a manner selected from the group consisting of manually, semi-automatically, fully automatically, and a combination thereof, and involves operation of components, mechanisms, and elements, in a manner selected from the group consisting of manual, semi-automatic, fully automatic, and a combination thereof. Moreover, according to actual steps and sub-steps, components, mechanisms, and elements, used for implementing a particular embodiment of the disclosed invention, steps and sub-steps are performed by using hardware, software, or an integrated combination thereof, and, components, mechanisms, and elements, operate by using hardware, software, or an integrated combination thereof.

In particular, software used for implementing the present invention features operatively connected and functioning written or printed data, in the form of software programs, software routines, software sub-routines, software symbolic languages, software code, software instructions or protocols, or a combination thereof. Hardware used for implementing the present invention features operatively connected and functioning electronic components and elements, in the form of a computer chip, an integrated circuit, an electronic circuit, an electronic sub-circuit, a hard-wired electrical circuit, or a combination thereof, involving digital and/or analog operations. Accordingly, an integrated combination of (1) software and (2) hardware, used for implementing the present invention, features an integrated combination of (1) operatively connected and functioning written or printed data, in the form of software programs, software routines, software sub-routines, software symbolic languages, software code, software instructions or protocols, or a combination thereof, and (2) operatively connected and functioning electronic components and elements, in the form of a computer chip, an integrated circuit, an electronic circuit, an electronic sub-circuit, a hard-wired electrical circuit, or a combination thereof, involving digital and/or analog operations.

BRIEF DESCRIPTION OF THE DRAWINGS

The present invention is herein described, by way of example only, with reference to the accompanying drawings. With specific reference now to the drawings in detail, it is stressed that the particulars shown are by way of example and for purposes of illustrative description of the preferred embodiments of the present invention only, and are presented in the cause of providing what is believed to be the most useful and readily understood description of the principles and conceptual aspects of the present invention. In this regard, no attempt is made to show structural details of the present invention in more detail than is necessary for a fundamental understanding of the invention, the description taken with the drawings making apparent to those skilled in the art how the several forms of the invention may be embodied in practice. In the drawings.

DESCRIPTION OF THE PREFERRED EMBODIMENTS

Figure 1:
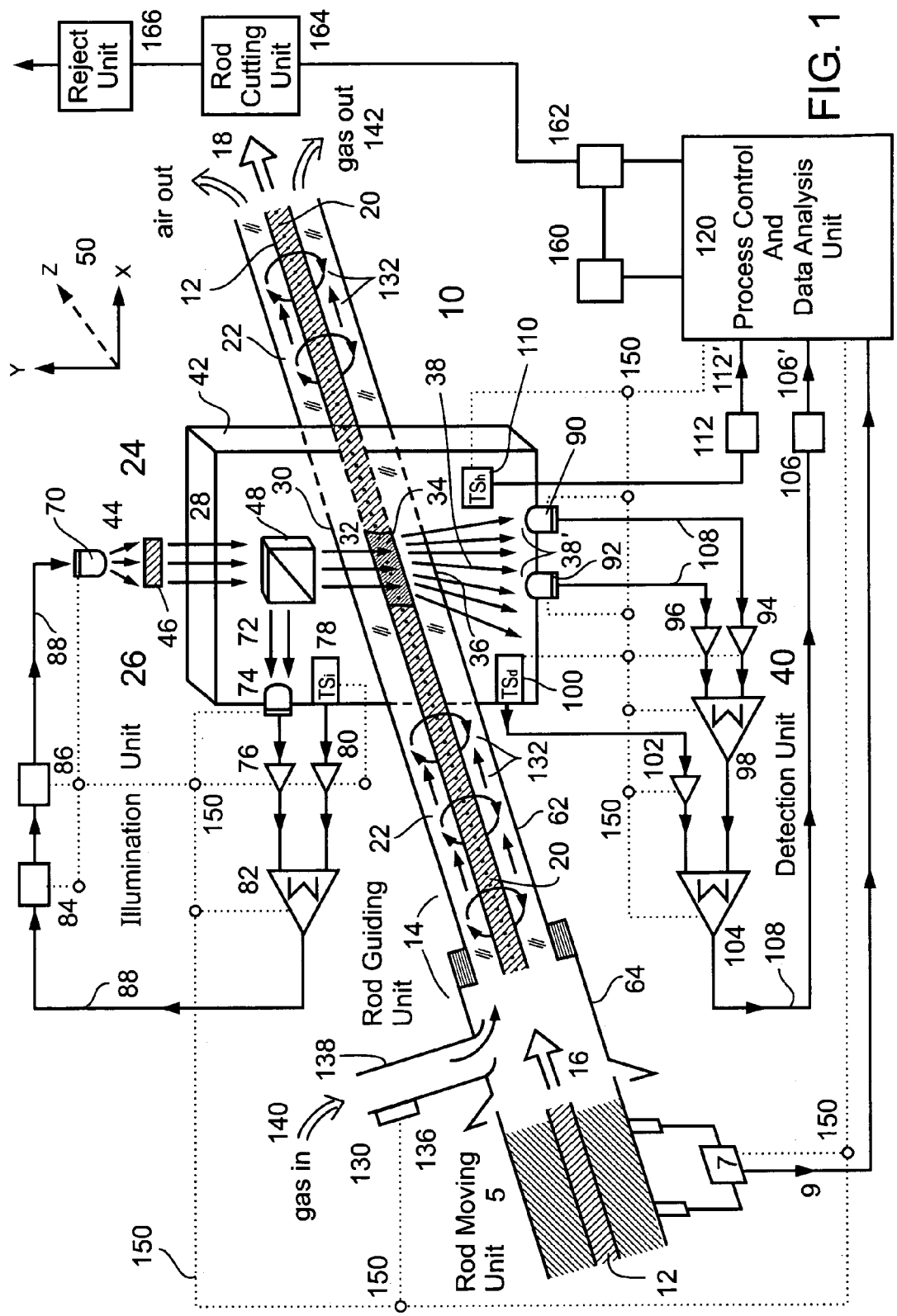
FIG. 1 is a schematic diagram illustrating a partially perspective cut-away sectional view of the first exemplary specific preferred embodiment of the generalized device for electro-optically inspecting and determining internal properties and characteristics of a longitudinally moving rod of material, in accordance with the present invention.

The present invention relates to a method and device for electro-optically inspecting and determining internal properties and characteristics, such as density, structure, defects, and impurities, and variabilities thereof, of a longitudinally moving rod of material. The rod of material is continuously or intermittently moving along its longitudinal axis while a focused beam of electromagnetic radiation is incident upon, measurably affected by, and transmitted through, volumetric segments of the longitudinally moving rod of material, along with detecting the transmitted electromagnetic radiation beam, during the electro-optical inspection process of measuring and analyzing the internal properties and characteristics of the longitudinally moving rod of material.

Steps, sub-steps, components, elements, operation, and implementation of a method and device for electro-optically inspecting and determining internal properties and characteristics, such as density, structure, defects, and impurities, and variabilities thereof, of a longitudinally moving rod of material, according to the present invention, are better understood with reference to the following description and accompanying drawings. Throughout the following description and accompanying drawings, same reference numbers refer to same components or same elements.

In the following description of the method and device of the present invention, included are main or principal steps and sub-steps, and main or principal devices, mechanisms, components, and elements, needed for sufficiently understanding proper 'enabling' utilization and implementation of the disclosed method and device. Accordingly, description of various possible required and/or optional preliminary, intermediate, minor, steps, sub-steps, devices, mechanisms, components, and/or elements, which are readily known by one of ordinary skill in the art, and/or which are available in the prior art and technical literature relating to electro-optically inspecting a longitudinally moving rod of material, and relating to principles and practice of electro-optics, are at most only briefly indicated herein.

It is to be understood that the present invention is not limited in its application to the details of the order or sequence, and number, of steps and sub-steps of operation or implementation of the method, or to the details of type, composition, construction, arrangement, order, and number, of the components and elements of the device, set forth in the following description, accompanying drawings, or examples. For example, the following description refers to a reference XYZ coordinate system 50, in order to illustrate implementation of the present invention. Other appropriate three-dimensional curvilinear coordinate systems, such as a cylindrical coordinate system, is also useable as reference for illustrating the present invention. The present invention is capable of other embodiments or of being practiced or carried out in various ways. Although steps, components, and materials, similar or equivalent to those described herein can be used for practicing or testing the present invention, suitable steps, components, and materials, are described herein.

It is also to be understood that unless otherwise defined, all technical and scientific words, terms, and/or phrases, used herein have either the identical or similar meaning as commonly understood by one of ordinary skill in the art to which this invention belongs. Phraseology, terminology, and, notation, employed herein are for the purpose of description and should not be regarded as limiting. Additionally, as used herein, the term 'about' refers to ±10% of the associated value.

Herein, internal properties and characteristics, such as density, structure, defects, and impurities, and variabilities thereof, of a longitudinally moving rod of material refer to the global, bulk, or macroscopic, internal properties and characteristics, such as density, structure, defects, and impurities, and variabilities thereof, of a specified volumetric segment or number of volumetric segments of the material, including bulk or macroscopic volume occupied by air and moisture throughout the material, making up or forming the longitudinally moving rod of material. These internal properties and characteristics of the longitudinally moving rod are to be clearly distinguished from the local, molecular, or microscopic, properties and characteristics, such as molecular density, molecular structure, microscopic defects, and microscopic impurities, and variabilities thereof, of only the material, excluding bulk or macroscopic volume occupied by air and moisture, making up or forming the longitudinally moving rod of material.

For example, internal properties and characteristics, such as density, structure, defects, and impurities, and variabilities thereof, of a longitudinally moving cigarette rod consisting of processed tobacco inside a rolled and sealed tube of cigarette wrapping paper, refer to the global, bulk, or macroscopic, density, structure, defects, and impurities, and variabilities thereof, of a specified volumetric segment or number of volumetric segments of the processed tobacco, including bulk or macroscopic volume occupied by air and moisture throughout the processed tobacco, inside the rolled and sealed tube of cigarette wrapping paper. These internal properties and characteristics of the longitudinally moving cigarette rod are to be clearly distinguished from the molecular density, molecular structure, microscopic defects, and microscopic impurities, and variabilities thereof, of only the processed tobacco molecules, excluding bulk or macroscopic volume occupied by air and moisture, making up or forming the longitudinally moving cigarette rod.

Herein, the phrase 'electro-optical transmission module' refers to a self-contained electro-optical device or assembly having a plurality of operatively connected electrical, electronic, optical, and electro-optical or opto-electrical, components, elements, and appropriate circuitry, connections, and linkages, thereof, which is designed, structured, and functional, as a module. As disclosed herein, the electro-optical transmission module performs electro-optical functions, involving digital and/or analog operations, described in the form of steps and sub-steps, for generating a focused beam of electromagnetic radiation which becomes incident upon a longitudinally moving rod of material, for illuminating volumetric segments of the longitudinally moving rod of material by the incident focused beam, such that at least part of the incident focused beam is affected by and transmitted through volumetric segments of the longitudinally moving rod of material, and for detecting the transmitted electromagnetic radiation beam, during the electro-optical inspection process of measuring and analyzing internal properties and characteristics of the longitudinally moving rod of material.

In other words, the electro-optical transmission module as herein illustratively described, is specifically designed, structured, and functional, for electro-optically transmitting electromagnetic radiation beams through a longitudinally moving rod of material, and for electro-optically detecting the affected transmitted electromagnetic radiation beams thereof. Moreover, the electro-optical transmission module of the present invention is designed, structured, and functional, for being connectable to, and operable with, one or more other elements, components, mechanisms, devices, units, and/or systems.

The electro-optical transmission module of the present invention is to be clearly distinguished from an electro-optical device or assembly, which may be in a modular form, which is specifically designed, structured, and functional, for electro-optically generating a focused beam of electromagnetic radiation which becomes incident upon a moving rod of material, such as a longitudinally moving rod of material, for illuminating the outer or exposed surface (and not internal volumetric segments) of the longitudinally moving rod of material by the incident focused beam, such that at least part of the incident focused beam is affected and reflected by (and not transmitted through), the outer or exposed surface of the longitudinally moving rod of material, and for detecting the reflected electromagnetic radiation beam, during an electro-optical inspection process of measuring and analyzing external (and not internal) properties and characteristics of the longitudinally moving rod of material.

Immediately following, there is first a listing of the main steps of the generalized method, and of the main components of the corresponding generalized device for implementing thereof, of the present invention. Thereafter, are highlighted main aspects of novelty and inventiveness, and, beneficial and advantageous features and characteristics, of the present invention. Thereafter, are illustratively described the steps and sub-steps of the generalized method, and the components, elements, operation, and implementation, of the generalized device, of the present invention, with reference to two exemplary specific preferred embodiments of the generalized device of the present invention.

The generalized method for electro-optically inspecting and determining internal properties and characteristics of a longitudinally moving rod of material, herein, also referred to as the generalized electro-optical inspection method, of the present invention, includes the main steps of: (a) guiding the longitudinally moving rod of material along its longitudinal axis by a rod guiding unit, along an optical path within a transparent passageway, the optical path and the transparent passageway coaxially extend along the longitudinal axis of the moving rod of material and pass through an electro-optical transmission module; (b) generating a focused beam of electromagnetic radiation by an illumination unit of the electro-optical transmission module, such that the focused beam is transmitted through a first side of the transparent passageway and incident upon the rod of material longitudinally moving within the transparent passageway; (c) illuminating a volumetric segment of the longitudinally moving rod of material by the incident focused beam, such that at least part of the incident focused beam is affected by and transmitted through the volumetric segment and then transmitted through a second side of the transparent passageway, for forming a rod material volumetric segment transmitted beam; and (d) detecting the rod material volumetric segment transmitted beam by a detection unit of the electro-optical transmission module, for forming a detected rod material volumetric segment transmitted beam useable for determining the internal properties and characteristics of the longitudinally moving rod of material.

For achieving higher sensitivity, signal to noise ratios, accuracy, and precision, and therefore, overall performance, of step (b)—generating the incident focused beam of electromagnetic radiation by the illumination unit, and/or of step (d)—detecting the rod material volumetric segment transmitted beam by the detection unit, in the generalized electro-optical inspection method, preferably, in a specific preferred embodiment of the generalized electro-optical inspection method, step (b) and/or step (d) further includes sub-steps and procedures, implemented via corresponding algorithms and software programs, and components for performing thereof, in particular, at least one strategically located temperature sensor, such as a thermocouple, and associated electro-optical circuitry, for monitoring temperature and compensating for temperature changes in critical regions of operation of the illumination unit and the detection unit of the electro-optical transmission module of the electro-optical inspection device. Such critical regions of operation are particularly in the immediate vicinity of the electro-optically inspected volumetric segment of the rod of material longitudinally moving along the optical path within the transparent passageway, during the electro-optical inspection process.

For achieving even higher sensitivity, signal to noise ratios, accuracy, and precision, and therefore, overall performance, of steps (a) through (d) in the generalized electro-optical inspection method, preferably, a specific preferred embodiment of the generalized electro-optical inspection method further includes sub-steps and procedures, and components for performing thereof, for preventing, eliminating, or at least reducing, radially directed vibrating of the longitudinally moving rod of material, in general, and of the electro-optically inspected volumetric segment of the longitudinally moving rod of material, in particular, during the electro-optical inspection process. In particular, preferably, following step (a) and preceding step (b) in the generalized electro-optical inspection method of the present invention, there is inserted the step of generating a continuous vortical type of flow of gas within and along the transparent passageway by a vortex generating mechanism, preferably, included as a component of the rod guiding unit, such that the flowing gas rotates as a vortex around the optical path and around the moving rod of material, and flows downstream within and along the transparent passageway in the same longitudinal direction of the moving rod of material, such that the flowing gas radially impinges upon the longitudinally moving rod of material within the transparent passageway. The flowing gas radially impinging upon the longitudinally moving rod of material prevents, eliminates, or reduces, radially directed vibrating of the longitudinally moving rod of material during the steps (a) through (d), during the electro-optically inspecting and determining the internal properties and characteristics of the longitudinally moving rod of material.

A specific preferred embodiment of the generalized electro-optical inspection method, of the present invention, further includes step (e): processing and analyzing the focused beam of step (b), the incident focused beam of step (c), and the rod material detected volumetric segment transmitted beam of step (d), by a process control and data analysis unit, for determining the internal properties and characteristics, such as density, structure, defects, and impurities, and variabilities thereof, of the longitudinally moving rod of material. Optionally, a specific preferred embodiment of the generalized electro-optical inspection method further includes step (f): controlling longitudinal movement of the longitudinally moving rod of material, by the process control and data analysis unit operatively connected to a rod moving unit, where the rod moving unit is operatively connected to the rod guiding unit, and the rod moving unit longitudinally moves the rod of material along its longitudinal axis.

The corresponding generalized device for electro-optically inspecting and determining internal properties and characteristics of a longitudinally moving rod of material, herein, also referred to as the generalized electro-optical inspection device, of the present invention, includes the main components: (a) a rod guiding unit for guiding the longitudinally moving rod of material along its longitudinal axis, along an optical path within a transparent passageway, the optical path and the transparent passageway coaxially extend along the longitudinal axis of the moving rod of material; and (b) an electro-optical transmission module through which pass the optical path and the transparent passageway, the electro-optical transmission module includes: (i) an illumination unit for generating a focused beam of electromagnetic radiation, such that the focused beam is transmitted through a first side of the transparent passageway and incident upon the rod of material longitudinally moving within the transparent passageway, the incident focused beam illuminates a volumetric segment of the longitudinally moving rod of material, such that at least part of the incident focused beam is affected by and transmitted through the volumetric segment and then transmitted through a second side of the transparent passageway, for forming a rod material volumetric segment transmitted beam; and (ii) a detection unit for detecting the rod material volumetric segment transmitted beam, for forming a detected rod material volumetric segment transmitted beam useable for determining the internal properties and characteristics of the longitudinally moving rod of material.

For achieving high speed, sensitivity, signal to noise ratios, accuracy, and precision, and therefore, overall performance, of the illumination unit for generating the focused beam and the incident focused beam of electromagnetic radiation, and of the detection unit for detecting the rod material volumetric segment transmitted beam, in the generalized electro-optical inspection device, preferably, in a specific preferred embodiment of the generalized electro-optical inspection device, each of the illumination unit, the detection unit, and preferably, a housing of selected components of these units, includes components, in particular, at least one strategically located temperature sensor, such as a thermocouple, and associated electro-optical circuitry, and, sub-steps and procedures, implemented via corresponding algorithms and software programs, for operating thereof, for monitoring temperature and compensating for temperature changes in critical regions of operation of the illumination unit and the detection unit of the electro-optical transmission module of the electro-optical inspection device. Such critical regions of operation are particularly in the immediate vicinity of the electro-optically inspected volumetric segment of the rod of material longitudinally moving along the optical path within the transparent passageway, during the electro-optical inspection process.

For achieving even higher sensitivity, signal to noise ratios, accuracy, and precision, and therefore, overall performance, of operation of the rod guiding unit and of the electro-optical transmission module in the generalized electro-optical inspection device, preferably, in a specific preferred embodiment of the generalized electro-optical inspection device, the rod guiding unit further includes components, and, sub-steps and procedures for operating thereof, for preventing, eliminating, or at least reducing, radially directed vibrating of the longitudinally moving rod of material, in general, and of the electro-optically inspected volumetric segment of the longitudinally moving rod of material, in particular, during the electro-optical inspection process.

In particular, preferably, the rod guiding unit in the generalized device of the present invention further includes a vortex generating mechanism, for generating a continuous vortical type of flow of gas within and along the transparent passageway, such that the flowing gas rotates as a vortex around the optical path and around the moving rod of material, and flows downstream within and along the transparent passageway in the same longitudinal direction of the moving rod of material, such that the flowing gas radially impinges upon the longitudinally moving rod of material within the transparent passageway. The flowing gas radially impinging upon the longitudinally moving rod of material prevents, eliminates, or reduces, radially directed vibrating of the longitudinally moving rod of material during operation of the rod guiding unit and during operation of the electro-optical transmission module, during the electro-optically inspecting and determining of the internal properties and characteristics of the longitudinally moving rod of material.

A specific preferred embodiment of the generalized electro-optical inspection device, of the present invention, further includes component (c): a process control and data analysis unit, which functions for (1) controlling the illumination unit, and selected components thereof, and the detection unit, and selected components thereof, of the electro-optical transmission module, and for (2) processing and analyzing the focused beam and the incident focused beam generated by the illumination unit, and the rod material detected volumetric segment transmitted beam detected by the detection unit, for determining the internal properties and characteristics, such as density, structure, defects, and impurities, and variabilities thereof, of the longitudinally moving rod of material. Optionally, in a specific preferred embodiment of the generalized electro-optical inspection device, the process control and data analysis unit also functions for (3) controlling a rod moving unit, operatively connected to the rod guiding unit, where the rod moving unit longitudinally moves the rod of material along its longitudinal axis.

A main aspect of novelty and inventiveness of the present invention is that it is based on using electro-optics for inspecting and determining internal properties and characteristics, such as density, structure, defects, and impurities, and variabilities thereof, of a longitudinally moving rod of material, and is fully applicable for inclusion in a commercial production or manufacturing sequence. This is accomplished by implementing the herein disclosed electro-optical inspection method and device, wherein the rod of material is continuously or intermittently moving along its longitudinal axis while at least one focused beam of electromagnetic radiation is incident upon, measurably affected by, and transmitted through, volumetric segments of the longitudinally moving rod of material, along with detecting the transmitted electromagnetic radiation beam, during the electro-optical inspection process of measuring and analyzing the internal properties and characteristics of the longitudinally moving rod of material.

This is in strong contrast to prior art teachings of methods, devices, and systems, for electro-optically inspecting and determining 'external' (and not 'internal') properties and characteristics, such as uniformity, structure, color, print, closures, openings, defects (for example, holes, defective and/or missing components), and impurities, and variabilities thereof, of or on the 'outer or exposed surface' (and not of or in a specified 'volumetric segment' or number of 'volumetric segments') of a continuously or intermittently moving rod of material, where the rod of material is continuously or intermittently moving sideways along or rolling around its 'radial' axis (and not moving along its 'longitudinal' axis), or is continuously or intermittently moving along its longitudinal axis, during the actual electro-optical inspection process. Such prior art is based on generating, detecting (collecting and measuring), and analyzing, light 'reflected by' (and not transmitted through) the outer or exposed surface of the continuously or intermittently moving rod of material.

Another main aspect of novelty and inventiveness of the present invention is that the disclosed electro-optical inspection method and device each includes sub-steps and procedures, implemented via corresponding algorithms and software programs, and components for performing thereof, in particular, at least one strategically located temperature sensor, such as a thermocouple, and associated electro-optical circuitry, for monitoring temperature and compensating for temperature changes in critical regions of operation of the illumination unit and the detection unit of the electro-optical transmission module of the electro-optical inspection device. Such critical regions of operation are particularly in the immediate vicinity of the electro-optically inspected volumetric segment of the rod of material longitudinally moving along the optical path within the transparent passageway, during the electro-optical inspection process. This enables achieving higher sensitivity, signal to noise ratios, accuracy, and precision, and therefore, overall performance, of generating the incident focused beam of electromagnetic radiation by the illumination unit of the electro-optical transmission module, and of detecting the rod material volumetric segment transmitted beam by the detection unit of the electro-optical transmission module.

Another main aspect of novelty and inventiveness of the present invention is that preferably, the disclosed electro-optical inspection method and device each includes sub-steps and procedures, and components for performing thereof, for preventing, eliminating, or at least reducing, radially directed vibrating of the longitudinally moving rod of material, in general, and of the electro-optically inspected volumetric segment of the longitudinally moving rod of material, in particular, during the electro-optical inspection process. In particular, preferably, the electro-optical inspection method and device each includes generating a continuous vortical type of flow of gas within and along the transparent passageway by a vortex generating mechanism, preferably, included as a component of the rod guiding unit, such that the flowing gas rotates as a vortex around the optical path and around the moving rod of material, and flows downstream within and along the transparent passageway in the same longitudinal direction of the moving rod of material, such that the flowing gas radially impinges upon the longitudinally moving rod of material within the transparent passageway. The flowing gas radially impinging upon the longitudinally moving rod of material prevents, eliminates, or reduces, radially directed vibrating of the longitudinally moving rod of material during operation of the rod guiding unit and during operation of the electro-optical transmission module, during the electro-optically inspecting and determining of the internal properties and characteristics of the longitudinally moving rod of material.

The electro-optical inspection method and device of the present invention have several beneficial and advantageous features and characteristics, which are based on, in addition to, or a consequence of, the above described main aspects of novelty and inventiveness.

First, the present invention is generally applicable for inspecting and determining internal properties and characteristics of a variety of different types of a rod of material, as long as the rod of material exhibits the behavior that an incident focused beam of electromagnetic radiation, while not altering the rod of material, is affected by and transmittable through volumetric segments of the rod of material. For example, but not limited to, a cigarette rod consisting of processed tobacco inside a rolled and sealed tube of cigarette wrapping paper.

Second, the present invention is directed to commercial applications requiring real time, non-invasive, high speed, high sensitivity, low noise, high accuracy, high precision, temperature compensative, and low vibration, measuring and analyzing of internal properties and characteristics of a continuously or intermittently longitudinally moving rod of material, as the rod of material is transported or conveyed during a commercial manufacturing sequence, particularly a manufacturing sequence including quality control and/or quality assurance processes. For example, in the case of manufacturing cigarettes, the present invention is directly applicable for inclusion as part of an overall commercial cigarette manufacturing sequence, during which bulk quantities of cut and processed tobacco leaves, along with any number of cigarette tobacco additives or ingredients, exiting an upstream manufacturing process are rolled, wrapped, and sealed, inside cigarette wrapping paper, and continuously or intermittently longitudinally transported or conveyed, for example, at a speed of between about 5 to 20 meters per second, as long, narrow, continuous tobacco filled cylinders or rods prior to entering further downstream processes, including for example, a cigarette rod cutting process, and a rod segment rejecting process, eventually leading to production of bulk quantities of individually cut, wrapped, and non-filtered or filtered, cigarettes in a box, for example, at a rate of about 10,000 cigarettes per minute.

Third, the present invention features modularity, based on design, construction, and operation, of the electro-optical inspection device, and operation thereof, in general, with respect to the electro-optical transmission module, in particular, through which passes the optical path within the transparent passageway. More specifically, it is straightforward to extend the present invention from an embodiment having a single electro-optical transmission module, operative with a single synchronized paired or coupled illumination unit/detection unit, to a larger embodiment having a plurality of electro-optical transmission modules, each fully operative with its own synchronized paired or coupled illumination unit/detection unit, and housing thereof, through which passes the same transparent passageway within which is the same coaxial optical path along which the longitudinally moving rod of material is guided by the rod guiding unit.

Fourth, in such a larger embodiment, each of the plurality of electro-optical transmission modules is positionable at a different longitudinal position or location around and along the same transparent passageway within which extends the same coaxial optical path, and is positionable at either the same or at a different angular, radial, or circumferential, position or location around the transparent passageway. More specifically, this is accomplished by spatially staggering or displacing the longitudinally and angular, radial, or circumferential, positions or locations of the electro-optical transmission modules relative to each other, and relative to the same transparent passageway within which extends the same coaxial optical path of the longitudinally moving rod of material.

An embodiment having spatially staggered or displaced positions or locations of a plurality of electro-optical transmission modules significantly decreases potential cross interferences among the various electromagnetic radiation beams emanating from, propagating through, transmitted into, out of, or through, and, entering into or exiting out of, the illumination units, the first and second side of the transparent passageway, the volumetric segments of the moving rod of material, and the detection units, of the plurality of electro-optical transmission modules. Additionally, spatially staggering or displacing the positions or locations of two or more electro-optical transmission modules enables each volumetric segment of the longitudinally moving rod of material to be inspected for a sufficiently integratable amount of time by the synchronized paired or coupled illumination unit/detection unit of each electro-optical transmission module. These factors contribute to achieving higher speed, sensitivity, signal to noise ratios, accuracy, and precision, and therefore, overall performance, of such a larger embodiment of the electro-optical inspection method and device, compared to an embodiment of the electro-optical inspection method and device having a single electro-optical transmission module.

Fifth, the present invention is highly flexible, in that the electro-optical transmission module, in general, and, the paired or coupled illumination unit/detection unit thereof, in particular, are totally functional by using different types of electrical, electronic, optical, and electro-optical or opto-electrical, components, elements, and appropriate circuitry, connections, and linkages, thereof, for example, based on either light emitting diode (LED) technology or fiber optic technology, which are designed, structured, and functional, as a module, and perform the herein described electro-optical functions, involving digital and/or analog operations.

Sixth, the present invention is highly flexible, in that it is operable according to different temporal modes, involving continuous or discontinuous operation of the electro-optical transmission module, in general, and, of the paired or coupled illumination unit/detection unit thereof, in particular, during the electro-optical inspection of the longitudinally moving rod of material.

More specifically, while the longitudinally moving rod of material is continuously or intermittently moving and being guided through a single electro-optical transmission module, or through a plurality of electro-optical transmission modules, the corresponding illumination units and detection units are continuously or discontinuously activated according to a pre-determined timing or switching schedule or sequence, in particular, via applying an appropriate synchronous or asynchronous on/off switching schedule or sequence for operating the illumination units and detection units. Additionally and/or alternatively, the electro-optical inspection device is connectable to and operable with a process control and data analysis unit, which is capable of controlling any of the steps and sub-steps, and components for performing thereof, and is capable of analyzing the rod material volumetric segment based data and information obtained therefrom, according to a spatially staggered configuration, a temporally continuous or discontinuous mode, and/or a combination thereof, in real time during the electro-optical inspection process of measuring and analyzing the internal properties and characteristics of the longitudinally moving rod of material.

Based upon the above described aspects of novelty and inventiveness, and, beneficial and advantageous features and characteristics, the present invention successfully addresses and overcomes limitations, and widens the scope, of prior art teachings of electro-optically inspecting a longitudinally moving rod of material.

Figure 2:
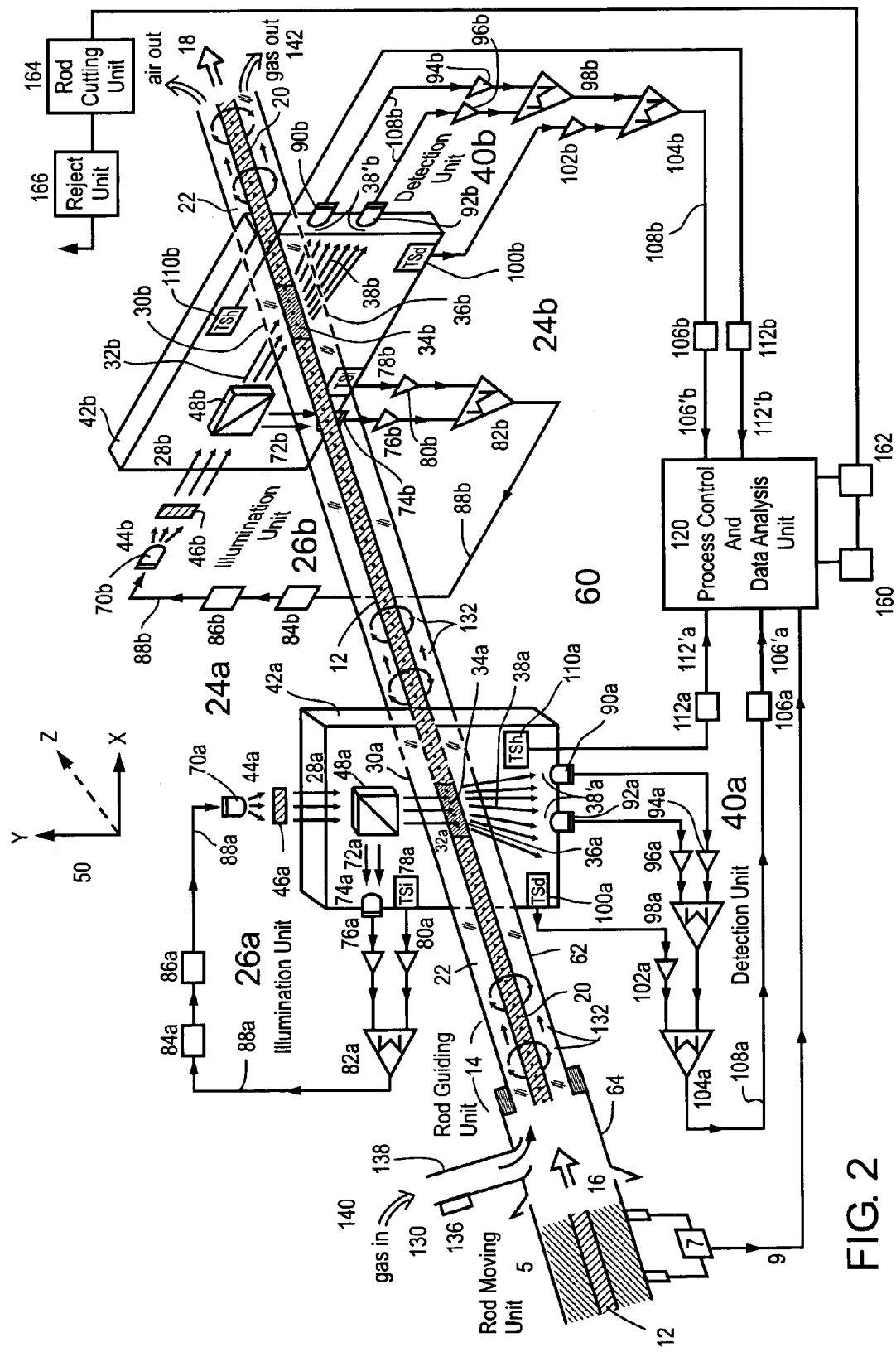
FIG. 2 is a schematic diagram illustrating a partially perspective cut-away sectional view of the second exemplary specific preferred embodiment of the generalized device for electro-optically inspecting and determining internal properties and characteristics of a longitudinally moving rod of material, in accordance with the present invention.

Following are illustratively described the steps and sub-steps of the generalized electro-optical inspection method, and the components, elements, operation, and implementation, of the generalized electro-optical inspection device, for electro-optically inspecting and determining internal properties and characteristics, such as density, structure, defects, and impurities, and variabilities thereof, of a longitudinally moving rod of material, of the present invention, with reference to two exemplary specific preferred embodiments of the generalized electro-optical inspection device, as illustrated in FIGS. 1 and 2.

In the following illustrative description, same reference numbers refer to same units, same components, or same elements. For particularly understanding and viewing the second exemplary specific preferred embodiment of the generalized electro-optical inspection device illustrated in FIG. 2, relative to the first exemplary specific preferred embodiment illustrated in FIG. 1, in FIG. 2, each unit, component, or element, which appears and is referenced as a unit, component, or element, that 'is part' of a plurality of the same units, components, or elements, is assigned a reference number with a letter suffix, that is, with an 'a' or 'b', with the same corresponding numerical reference number as used for describing that same unit, component, or element, which appears and is referenced in FIG. 1. Accordingly, in FIG. 2, each unit, component, or element, which appears or is referenced as a unit, component, or element, that 'is not part' of a plurality of the same units, components, or elements, respectively, is assigned a reference number 'without' a letter suffix, that is, without an 'a' or 'b', and corresponds to the same numerical reference number as used for describing that same unit, component, or element, which appears and is referenced in FIG. 1.

Thus, it is to be clearly understood, that unless otherwise stated, description of the structure and function, and method of implementing or operating, of each unit, component, and element, of the first exemplary specific preferred embodiment of the generalized electro-optical inspection device illustrated in FIG. 1, as example, is fully and equally applicable to the correspondingly same unit, component, and element, respectively, of the second exemplary specific preferred embodiment of the generalized electro-optical inspection device illustrated in FIG. 2. Repetition of description of the present invention occurs where considered appropriate for properly and fully understanding the similarities and differences between the first and second exemplary specific preferred embodiments of the generalized electro-optical inspection device illustrated in FIGS. 1 and 2, and method of implementing or operating each embodiment thereof.

As illustrated in FIG. 1, a schematic diagram illustrating a partially perspective cut-away sectional view of the first exemplary specific preferred embodiment of the generalized device, hereinafter, referred to as electro-optical inspection device 10, for electro-optically inspecting and determining internal properties and characteristics of a longitudinally moving rod of material, hereinafter, for brevity, also referred to as moving rod of material 12, or more briefly, rod of material 12, electro-optical inspection device 10 includes a single electro-optical transmission module 24 through which passes the transparent passageway 22, within which is the coaxial optical path 20 along which the longitudinally moving rod of material 12 is guided by the rod guiding unit 14.

As illustrated in FIG. 2, a schematic diagram illustrating a partially perspective cut-away sectional view of the second exemplary specific preferred embodiment of the generalized device, hereinafter, referred to as electro-optical inspection device 60, for electro-optically inspecting and determining internal properties and characteristics of a longitudinally moving rod of material, electro-optical inspection device 60 includes an exemplary plurality of two electro-optical transmission modules 24, that is 24a and 24b, through which passes the same transparent passageway 22, within which is the same coaxial optical path 20 along which the longitudinally moving rod of material 12 is guided by the rod guiding unit 14.

As clearly shown in FIG. 2, with reference to reference XYZ coordinate system 50, in electro-optical inspection device 60, the longitudinal and angular, radial, or circumferential, positions or locations of the two electro-optical transmission modules 24a and 24b, in general, and the units of each respective module, in particular, relative to each other, and relative to the same transparent passageway 22 within which extends coaxial optical path 20, are spatially staggered or displaced along the same coaxial optical path 20, along which the longitudinally moving rod of material 12 is guided by the rod guiding unit 14. This translates to achieving higher speed, sensitivity, signal to noise ratios, accuracy, and precision, and therefore, overall performance, of the electro-optical inspection method implemented by using electro-optical inspection device 60, having two electro-optical transmission modules 24a and 24b, in the second exemplary specific preferred embodiment illustrated in FIG. 2, compared to using electro-optical inspection device 10, having a single electro-optical transmission module 24, in the first exemplary specific preferred embodiment illustrated in FIG. 1, of the generalized electro-optical inspection device for electro-optically inspecting and determining internal properties and characteristics of the longitudinally moving rod of material 12.

Throughout the following illustrative description of the first and second exemplary specific preferred embodiments of the generalized device for electro-optically inspecting and determining internal properties and characteristics of a longitudinally moving rod of material, of the present invention, as illustrated in FIGS. 1 and 2, respectively, it is to be clearly understood that electro-optical inspection device 10 (FIG. 1), including the single electro-optical transmission module 24 through which passes the transparent passageway 22, and electro-optical inspection device 60 (FIG. 2), including the two electro-optical transmission modules 24a and 24b through which passes the same transparent passageway 22, correspond to two different, but generically related, exemplary specific preferred embodiments 'of the same' generalized electro-optical inspection device, implemented according 'to the same' generalized electro-optical inspection method, of the present invention, and do not correspond to two different, unrelated and/or independent devices.

As shown in each of FIGS. 1 and 2, moving rod of material 12 is longitudinally moved along its longitudinal axis by a rod moving unit 5. In FIGS. 1 and 2, with reference to reference XYZ coordinate system 50, it is to be viewed and understood that the longitudinal direction of movement of moving rod of material 12 is, for example, in the Z-direction and is coaxial with the longitudinal axis of moving rod of material 12, extending between rod material entrance area 16 and rod material exit area 18 (indicated in FIGS. 1 and 2 by the straight and hollow open-tail reference arrows on the lower left side and on the upper right side, respectively) of rod guiding unit 14 in each electro-optical inspection device 10 and electro-optical inspection device 60, respectively.

As shown in FIGS. 1 and 2, rod moving unit 5 provides and supplies longitudinally moving rod of material 12 to each of electro-optical inspection device 10 and electro-optical inspection device 60, respectively, via rod material entrance area 16. For example, in the case of manufacturing cigarettes, each of electro-optical inspection device 10 and electro-optical inspection device 60, of the present invention, is directly applicable for inclusion as part of an overall commercial cigarette manufacturing sequence. In such an overall commercial cigarette manufacturing sequence, bulk quantities of cut and processed tobacco leaves, along with any number of cigarette tobacco additives or ingredients, exiting an upstream manufacturing process are rolled, wrapped, and sealed, inside cigarette wrapping paper, and continuously or intermittently longitudinally transported or conveyed by a rod moving system, device, or mechanism, such as rod moving unit 5, for example, at a speed of between about 5 to 20 meters per second, as long, narrow, continuous tobacco filled cylinders or rods prior to entering further downstream processes, including for example, a cigarette rod cutting process, and a rod section or segment rejecting process, eventually leading to production of bulk quantities of individually cut, wrapped, and non-filtered or filtered, cigarettes in a box, for example, at a rate of about 10,000 cigarettes per minute.

Automatic operation of rod moving unit 5, including for example, control of the linear speed at which rod moving unit 5 moves rod of material 12 along its longitudinal axis to each electro-optical inspection device 10 and 60, respectively, via rod material entrance area 16 is performed by a process control and data analysis unit, such as process control and data analysis unit 120. Preferably, rod moving unit 5 either includes, or is operatively connected to, a rod moving unit mechanism 7, which provides a real time rod moving unit clock output signal 9, that includes data and information about the rate or linear speed at which rod moving unit 5 moves rod of material 12.

In Step (a) of the generalized electro-optical inspection method for electro-optically inspecting and determining internal properties and characteristics of a longitudinally moving rod of material, of the present invention, there is guiding the longitudinally moving rod of material along its longitudinal axis by a rod guiding unit, along an optical path within a transparent passageway, the optical path and the transparent passageway coaxially extend along the longitudinal axis of the moving rod of material and pass through an electro-optical transmission module.

In the first exemplary specific preferred embodiment of the generalized device for electro-optically inspecting and determining internal properties and characteristics of a longitudinally moving rod of material, that is, moving rod of material 12, as illustrated in FIG. 1, electro-optical inspection device 10 includes the main components: (a) a rod guiding unit 14, and (b) an electro-optical transmission module 24.

In electro-optical inspection device 10, rod guiding unit 14 is for guiding moving rod of material 12 along its longitudinal axis, extending between rod material entrance area 16 and rod material exit area 18 of electro-optical inspection device 10, along an optical path 20 (in FIG. 1, indicated by the dotted line 20 drawn along the length of moving rod of material 12) within a transparent passageway 22, where optical path 20 and transparent passageway 22 coaxially extend along the longitudinal axis of moving rod of material 12. Preferably, rod guiding unit 14 is operatively connected to a rod moving unit, such as rod moving unit 5, for receiving longitudinally moving rod of material 12 provided and supplied by rod moving unit 5, for example, via rod material entrance area 16.

Rod guiding unit 14 includes the main components: (i) a transparent housing 62, and (ii) a rod material entrance assembly 64.

In rod guiding unit 14, transparent housing 62 is for housing, holding, or confining, transparent passageway 22 within which is coaxial optical path 20, along which is guided longitudinally moving rod of material 12. Transparent housing 62 is, preferably, of a hollow tubular or cylindrical geometrical shape, and constructed from an optically transparent material, for example, a plastic, a glass, a transparent composite material, or a combination thereof.

Rod material entrance assembly 64 is operatively attached or connected to transparent housing 62, and functions as an entrance for the longitudinally moving rod of material 12 entering into electro-optical inspection device 10, via rod material entrance area 16. Preferably, rod material entrance assembly 64 is operatively connected to a rod moving unit, such as rod moving unit 5, thereby enabling operative connection of rod guiding unit 14 with rod moving unit 5. Rod material entrance assembly 64 is preferably of a mostly hollow tubular or cylindrical geometrical shape, and constructed from a metallic material, a non-metallic material, a composite material, or a combination thereof, for enabling operative attachment or connection to transparent housing 62 and for enabling guiding of the moving rod of material 12 along its longitudinal axis along optical path 20 within coaxial transparent passageway 22.

For proper implementation of the electro-optical inspection method and electro-optical inspection device 10, the optically transparent material of transparent housing 62 in rod guiding unit 14 is compatible with the properties, characteristics, and operation, of illumination unit 26. Especially, regarding wavelength or frequency, and intensity or power, of electromagnetic radiation source beam 44 generated by illumination unit 26, such that focused beam 28 is transmittable through first side 30 of transparent passageway 22 and subsequently incident upon volumetric segment 34 of rod of material 12 longitudinally moving within transparent passageway 22.

Moreover, this compatibility is such that subsequent to incident focused beam 32 illuminating volumetric segment 34 of moving rod of material 12, and subsequent to at least part of incident focused beam 32 being affected by and transmitted through volumetric segment 34, the affected incident focused beam exiting volumetric segment 34 is then transmittable through second side 36 of transparent passageway 22, for forming rod material volumetric segment transmitted beam 38. This in turn, enables detection of rod material volumetric segment transmitted beam 38, for forming detected rod material volumetric segment transmitted beam 38' useable for determining the internal properties and characteristics of the longitudinally moving rod of material 12.

In Step (b), there is generating a focused beam of electromagnetic radiation by an illumination unit of the electro-optical transmission module, such that the focused beam is transmitted through a first side of the transparent passageway and incident upon the rod of material longitudinally moving within the transparent passageway. In Step (c), there is illuminating a volumetric segment of the longitudinally moving rod of material by the incident focused beam, such that at least part of the incident focused beam is affected by and transmitted through the volumetric segment and then transmitted through a second side of the transparent passageway, for forming a rod material volumetric segment transmitted beam.

In electro-optical inspection device 10, as illustrated in FIG. 1, electro-optical transmission module 24 through which pass optical path 20 and transparent passageway 22, includes the main components: (i) an illumination unit 26, and (ii) a detection unit 40.

Illumination unit 26 is for generating a focused beam 28 of electromagnetic radiation, such that focused beam 28 is transmitted through a first side 30 of transparent passageway 22 and incident upon rod of material 12 longitudinally moving within transparent passageway 22, and the incident focused beam 32 illuminates a volumetric segment 34 of longitudinally moving rod of material 12, such that at least part of incident focused beam 32 is affected by and transmitted through volumetric segment 34 and then transmitted through a second side 36 of transparent passageway 22, for forming a rod material volumetric segment transmitted beam 38.

In a first specific configuration of illumination unit 26 in electro-optical transmission module 24 of electro-optical inspection device 10, illumination unit 26 includes the main components: (1) an electromagnetic radiation beam source 70, and (2) a focusing lens 46.

In the first specific configuration of illumination unit 26 in electro-optical transmission module 24 of electro-optical inspection device 10, illumination unit 26 'does not include' components, in particular, a polarizing beam splitter 48, at least one strategically located operatively coupled optical feedback reference beam detector 74 and illumination unit temperature sensor, $TS_i$, 78, and associated electro-optical feedback circuitry, and, sub-steps and procedures, implemented via corresponding algorithms and software programs, for operating thereof, for monitoring temperature and compensating for temperature changes in critical regions of operation of illumination unit 26 in electro-optical transmission module 24 of electro-optical inspection device 10.

Electromagnetic radiation beam source 70 generates and emits electromagnetic radiation source beam 44. Electromagnetic radiation beam source 70 is any appropriately compact or miniature sized and configured device, mechanism, or component, capable of generating and emitting an electromagnetic radiation source beam 44. Electromagnetic radiation beam source 70 is of structure and functions according to either light emitting diode (LED) technology, or fiber optic technology. For example, electromagnetic radiation beam source 70 is a light emitting diode (LED). Alternatively, electromagnetic radiation beam source 70 is an operative combination, for example, an integral device, of an electromagnetic radiation beam generator, for example, a lamp or a laser, and a fiber optic conductor or fiber optic guide.

In general, electromagnetic radiation source beam 44 generated and emitted by electromagnetic radiation beam source 70 is infrared radiation, visible light, or ultraviolet radiation. Preferably, for electro-optically inspecting and determining internal properties and characteristics, such as density, structure, defects, and impurities, and variabilities thereof, of a volumetric segment 34 of moving rod of material 12 being a cigarette rod, consisting of processed tobacco inside a rolled and sealed tube of cigarette wrapping paper, electromagnetic radiation source beam 44 is infrared radiation having wavelength in the range of between about 900 nm and about 1000 nm, and more preferably, having wavelength in the range of between about 920 nm and about 970 nm.

Focusing lens 46 is for focusing electromagnetic radiation source beam 44, for forming focused beam 28. In the first specific configuration of illumination unit 26 in electro-optical transmission module 24 of electro-optical inspection device 10, 'without inclusion' of a polarizing beam splitter 48 and other components of a temperature change monitoring and compensating electro-optical feedback loop in illumination unit 26, focused beam 28 becomes incident focused beam 32, which is transmitted through first side 30 of transparent passageway 22 and incident upon volumetric segment 34.

Incident focused beam 32 illuminates volumetric segment 34 of rod of material 12 longitudinally moving along coaxial optical path 20 within transparent passageway 22, such that at least part of incident focused beam 32 is affected by and transmitted through volumetric segment 34 and then transmitted through second side 36 of transparent passageway 22, for forming rod material volumetric segment transmitted beam 38. Rod material volumetric segment transmitted beam 38 is detected by a detection unit 40 in electro-optical transmission module 24 of electro-optical inspection device 10, for forming a detected rod material volumetric segment transmitted beam 38' useable for determining the internal properties and characteristics of the longitudinally moving rod of material 12, as described in further detail below.

While electro-optically inspecting longitudinally moving rod of material 12, temperature changes typically occur in critical regions of operation of illumination unit 26 in electro-optical transmission module 24 of electro-optical inspection device 10, particularly in the immediate vicinity of the electro-optically inspected volumetric segment 34 of moving rod of material 12. Magnitudes of such temperature changes may be sufficiently large so as to significantly increase noise and error levels during the illumination process, which may translate to meaningful decreases in accuracy and precision of the results obtained from the electro-optical inspection process.

For achieving higher sensitivity, signal to noise ratios, accuracy, and precision, and therefore, overall performance, of illumination unit 26 for generating focused beam 28 and incident focused beam 32 of electromagnetic radiation, in electro-optical transmission module 24 of electro-optical inspection device 10, preferably, illumination unit 26 further includes components, in particular, a polarizing beam splitter 48, at least one strategically located operatively coupled optical feedback reference beam detector 74 and illumination unit temperature sensor, $TS_i$, 78, and associated electro-optical feedback circuitry, and, sub-steps and procedures, implemented via corresponding algorithms and software programs, for operating thereof, for monitoring temperature and compensating for temperature changes in critical regions of operation of illumination unit 26 in electro-optical transmission module 24 of electro-optical inspection device 10. Such critical regions of operation are particularly in the immediate vicinity of the electro-optically inspected volumetric segment 34 of rod of material 12 longitudinally moving along optical path 20 within transparent passageway 22, during the electro-optical inspection process.

Accordingly, in a second specific, more preferred, configuration of illumination unit 26 in electro-optical transmission module 24 of electro-optical inspection device 10, illumination unit 26 includes the main components: (1) electromagnetic radiation beam source 70, and (2) focusing lens 46, and further includes additional main components: (3) a polarizing beam splitter 48, (4) an optical feedback reference beam detector 74, (5) an optical feedback reference beam signal amplifier 76, (6) an illumination unit temperature sensor, $TS_i$, 78, (7) an illumination unit temperature sensor signal amplifier 80, (8) an illumination unit signal comparator 82, (9) a proportional integrated (PI) regulator 84, (10) a current regulator 86, and (11) illumination unit electro-optical feedback loop component connections and linkages 88.

Focusing lens 46, as in the preceding description of the first specific configuration of illumination unit 26, is for focusing electromagnetic radiation source beam 44, for forming focused beam 28. In the second specific configuration of illumination unit 26 in electro-optical transmission module 24 of electro-optical inspection device 10, with inclusion of a polarizing beam splitter 48 and the other components, (4)-(11), of a temperature change monitoring and compensating electro-optical feedback loop in illumination unit 26, focused beam 28 propagates into polarizing beam splitter 48.

Polarizing beam splitter 48 is for splitting focused beam 28 into two separate beams, an optical feedback reference beam 72, and incident focused beam 32. Optical feedback reference beam 72 is fed back into the electro-optical circuit of illumination unit 26, via optical feedback reference beam detector 74, while incident focused beam 32 is transmitted through first side 30 of transparent passageway 22 and incident upon volumetric segment 34, thereby illuminating volumetric segment 34 of rod of material 12 longitudinally moving along coaxial optical path 20 within transparent passageway 22.

In general, the area of illumination, or illuminating area, of incident focused beam 32, directly originating from focused beam 28 without first passing through polarizing beam splitter 48 (in accordance with the first specific configuration of illumination unit 26), or originating from focused beam 28 after first passing through polarizing beam splitter 48 (in accordance with the second specific configuration of illumination unit 26), is of a variable magnitude, and is selected and used in accordance with the magnitude of the outer or external circumferential area of moving rod of material 12, and in accordance with the magnitude of the average or characteristic diameter of the smallest particles or substances making up rod of material 12, which are of analytical interest and inspected during the electro-optical inspection process. The area of illumination, or illuminating area, of incident focused beam 32 corresponds to the 'initial or frontal' area of moving rod of material 12 upon which incident focused beam 32 is incident.

In FIG. 1, with reference to reference XYZ coordinate system 50, it is shown that during operation of electro-optical inspection device 10, electromagnetic radiation source beam 44 generated by illumination unit 26 is focused, via focusing lens 46, in the negative Y-direction towards first side 30 (in FIG. 1, to be perspectively viewed and understood as from above and towards the top side) of transparent passageway 22 and is also incident, via polarizing beam splitter 48, in the negative Y-direction upon rod of material 12 longitudinally moving in the positive Z-direction along coaxial optical path 20 within transparent passageway 22. Incident focused beam 32 illuminates, in the negative Y-direction, volumetric segment 34 of longitudinally moving rod of material 12. Accordingly, the area of illumination, or illuminating area, of incident focused beam 32 corresponds to the 'initial or frontal' area (in FIG. 1, to be perspectively viewed and understood as the top side area) of volumetric segment 34 upon which incident focused beam 32 is incident.

Preferably, the magnitude of the area of illumination, or illuminating area, of incident focused beam 32 is less than the magnitude of the outer or external circumferential area of moving rod of material 12, and greater than the magnitude of the average or characteristic diameter of the smallest particles or substances making up rod of material 12, which are of analytical interest and inspected during the electro-optical inspection process. For example, preferably, for electro-optically inspecting and determining internal properties and characteristics of volumetric segments 34 of moving rod of material 12 being a cigarette rod, the magnitude of the area of illumination, or illuminating area, of incident focused beam 32 is less than the magnitude, typically, on the order of about 1 cm, of the outer or external circumferential area of the cigarette rod, and greater than the magnitude of the average or characteristic diameter, typically, on the order of about 4 mm, of the smallest particles or substances making up the cigarette rod, which are of analytical interest and inspected during the electro-optical inspection process.

Optical feedback reference beam detector 74 is for detecting and receiving optical feedback reference beam 72 output from polarizing beam splitter 48, and converting optical feedback reference beam 72 into a corresponding optical feedback reference beam output signal, which is sent back into the electro-optical circuit of illumination unit 26, via optical feedback reference beam signal amplifier 76.

Optical feedback reference beam detector 74 is any appropriately compact or miniature sized and configured device, mechanism, or component, capable of detecting and receiving electromagnetic radiation source beam 44 generated and emitted according to either light emitting diode (LED) technology, or fiber optic technology, and for converting such a detected and received beam into a corresponding output signal. For example, optical feedback reference beam detector 74 is of structure and functions as a light receiving type of device, mechanism, component, or element, such as a phototransistor, a photosensitive transducer, a fiber optic conductor or guide, or a photoelectric element. For process design, process control, and reference purposes, calibration data and information correlating a range of values of the input optical feedback reference beam 72 with a range of values of the corresponding optical feedback reference beam output signal, are empirically determined using standardized conditions of operating electro-optical transmission module 24.

Optical feedback reference beam signal amplifier 76 is for receiving the optical feedback reference beam output signal sent from optical feedback reference beam detector 74, and for amplifying the optical feedback reference beam output signal. The amplified optical feedback reference beam output signal is then sent to illumination unit signal comparator 82.

Illumination unit temperature sensor, $TS_i$, 78 is for monitoring and sensing the temperature, typically, in the range of between about 50° C. and 60° C., in the critical region of operation of illumination unit 26. As shown in FIG. 1, such critical region of operation is particularly in the immediate vicinity of the electro-optically inspected volumetric segment 34 of rod of material 12 longitudinally moving along optical path 20 within transparent passageway 22, during the electro-optical inspection process. More specifically, the critical region of operation is in the immediate vicinity where incident focused beam 32 is transmitted through first side 30 of transparent passageway 22 and incident upon volumetric segment 34, for illuminating volumetric segment 34 of rod of material 12 longitudinally moving along coaxial optical path 20 within transparent passageway 22.

Illumination unit temperature sensor, $TS_i$, 78 generates an illumination unit temperature sensor output signal proportional to the sensed temperature in the critical region of operation of illumination unit 26, and sends the illumination unit temperature sensor output signal back into the electro-optical circuit, herein, also referred to as the electro-optical feedback loop, of illumination unit 26, via illumination unit temperature sensor signal amplifier 80. In general, illumination unit temperature sensor, $TS_i$, 78 is any appropriately compact or miniature sized and configured temperature sensing device, mechanism, or component, for example, a thermocouple, capable of sensing temperature, and generating an electrical or electronic signal corresponding and proportional to the sensed temperature. For process design, process control, and reference purposes, calibration data and information correlating a range of values of the input sensed temperature with a corresponding range of values of the corresponding illumination unit temperature sensor output signal, are empirically determined using standardized conditions of operating electro-optical transmission module 24.

Illumination unit temperature sensor signal amplifier 80 is for receiving the illumination unit temperature sensor output signal sent from illumination unit temperature sensor, $TS_i$, 78, and for amplifying the illumination unit temperature sensor output signal. The amplified illumination unit temperature sensor output signal is sent to illumination unit signal comparator 82.

Illumination unit signal comparator 82 is for receiving the amplified optical feedback reference beam output signal sent from optical feedback reference beam signal amplifier 76, and for receiving the amplified illumination unit temperature sensor output signal sent from illumination unit temperature sensor signal amplifier 80. Illumination unit signal comparator 82 then compares, and adds or subtracts, in a compensative manner, the value of the amplified illumination unit temperature sensor output signal, to or from, respectively, the value of the amplified optical feedback reference beam output signal, according to the magnitude and the direction or sign (positive or negative) of the temperature change represented by the amplified illumination unit temperature sensor output signal, for generating an illumination unit signal comparator output signal, which is sent to proportional integrated (PI) regulator 84.

Proportional integrated (PI) regulator 84 is for receiving the illumination unit signal comparator output signal sent from illumination unit signal comparator 82, and for generating a proportional integrated (PI) regulator output signal, which is sent to current regulator 86.

Current regulator 86 is for receiving the proportional integrated (PI) regulator output signal sent from proportional integrated (PI) regulator 84, and for generating a current regulator output signal, which is sent to electromagnetic radiation beam source 70. In proportion to the magnitude of the proportional integrated (PI) regulator output signal, the current regulator output signal regulates, in a temperature compensative manner, the level of current used by electromagnetic radiation beam source 70, and therefore, regulates, in a temperature compensative manner, the generation and emission, via regulating wavelength or frequency, and intensity or power, of electromagnetic radiation source beam 44 by electromagnetic radiation beam source 70. For process design, process control, and reference purposes, calibration data and information correlating a range of values of the input proportional integrated (PI) regulator signal with a corresponding range of values of the corresponding current regulator output signal, are empirically determined using standardized conditions of operating electro-optical transmission module 24.

Illumination unit electro-optical feedback loop component connections and linkages 88 are for operatively connecting and linking the components, in particular, (1) electromagnetic radiation beam source 70, (4) optical feedback reference beam detector 74, (5) optical feedback reference beam signal amplifier 76, (6) illumination unit temperature sensor, $TS_i$, 78, (7) illumination unit temperature sensor signal amplifier 80, (8) illumination unit signal comparator 82, (9) proportional integrated (PI) regulator 84, and (10) current regulator 86, included in the second specific configuration of illumination unit 26 in electro-optical transmission module 24 of electro-optical inspection device 10, in the form of an electro-optical feedback loop, based on monitoring and compensating for temperature changes.

In the second specific configuration of illumination unit 26 in electro-optical transmission module 24 of electro-optical inspection device 10, the regulatory, temperature compensative, action performed by proportional integrated (PI) regulator 84 and current regulator 86 is based upon, and in accordance with, operation of the strategically located operatively coupled optical feedback reference beam detector 74 and temperature sensor, $TS_i$, 78, and associated electro-optical feedback circuitry, included in illumination unit 26, involving the illumination unit temperature sensor output signal sent by illumination unit temperature sensor 78, which in turn, is proportional to the sensed temperature in the critical region of operation of illumination unit 26. Thus, overall operation of illumination unit 26 is based on, and in accordance with, a temperature change monitoring and compensating electro-optical feedback loop.

Automatic operations of illumination unit 26, in general, and of the above described electrical and electronic components and elements thereof, in electro-optical transmission module 24 of electro-optical inspection device 10, are performed by a process control and data analysis unit, such as process control and data analysis unit 120.

In Step (d), there is detecting the rod material volumetric segment transmitted beam by a detection unit of the electro-optical transmission module, for forming a detected rod material volumetric segment transmitted beam useable for determining the internal properties and characteristics of the longitudinally moving rod of material.

As described above, according to operation of either the first or second specific configuration of illumination unit 26 in electro-optical transmission module 24 of electro-optical inspection device 10, incident focused beam 32 illuminates volumetric segment 34 of longitudinally moving rod of material 12, such that at least part of incident focused beam 32 is affected by and transmitted through volumetric segment 34 and then transmitted through second side 36 of transparent passageway 22, for forming rod material volumetric segment transmitted beam 38. In electro-optical transmission module 24 of electro-optical inspection device 10, detection unit 40 is for detecting rod material volumetric segment transmitted beam 38, for forming a detected rod material volumetric segment transmitted beam 38' useable for determining the internal properties and characteristics of the longitudinally moving rod of material 12.

In a first specific configuration of detection unit 40 in electro-optical transmission module 24 of electro-optical inspection device 10, detection unit 40 includes the main components: (1) a transmitted beam first detector 90, (2) a transmitted beam second detector 92, (3) a transmitted beam signal first amplifier 94, (4) a transmitted beam signal second amplifier 96, (5) a detection unit signal integrator 98, (6) a detection unit signal buffer 106, and (7) detection unit component connections and linkages 108.

In the first specific configuration of detection unit 40 in electro-optical transmission module 24 of electro-optical inspection device 10, detection unit 40 'does not include' components, in particular, at least one strategically located detection unit temperature sensor, $TS_d$, 100 and an operatively coupled detection unit signal comparator 104, and associated electro-optical circuitry, and, sub-steps and procedures, implemented via corresponding algorithms and software programs, for operating thereof, for monitoring temperature and compensating for temperature changes in critical regions of operation of detection unit 40 in electro-optical transmission module 24 of electro-optical inspection device 10.

Transmitted beam first detector 90 and transmitted beam second detector 92 are for detecting and receiving rod material volumetric segment transmitted beam 38 which is transmitted from volumetric segment 34 and then transmitted through second side 36 of transparent passageway 22, for forming detected rod material volumetric segment transmitted beam 38'. Transmitted beam first and second detectors 90 and 92, respectively, each convert part of detected rod material volumetric segment transmitted beam 38' into a corresponding detected rod material volumetric segment transmitted beam output signal, which is sent to transmitted beam signal first and second amplifiers 94 and 96, respectively.

Each of transmitted beam first and second detector 90 and 92 is any appropriately compact or miniature sized and configured device, mechanism, or component, capable of detecting and receiving rod material volumetric segment transmitted beam 38, and for converting such a detected and received beam into a corresponding output signal. For example, each of transmitted beam first and second detector 90 and 92 is of structure and functions as a light receiving type of device, mechanism, component, or element, such as a phototransistor, a photosensitive transducer, a fiber optic conductor or guide, or a photoelectric element. For process design, process control, and reference purposes, calibration data and information correlating a range of values of the input rod material volumetric segment transmitted beam 38 with a range of values of the corresponding detected rod material volumetric segment transmitted beam output signals, are empirically determined using standardized conditions of operating electro-optical transmission module 24.

Transmitted beam signal first amplifier 94 and transmitted beam signal second amplifier 96, are each for receiving a corresponding detected rod material volumetric segment transmitted beam output signal, sent from transmitted beam first and second detectors 90 and 92, respectively, and for amplifying the corresponding detected rod material volumetric segment transmitted beam output signal. The corresponding amplified detected rod material volumetric segment transmitted beam output signals are then sent to detection unit signal integrator 98.

Detection unit signal integrator 98 is for receiving, and integrating the values of, the corresponding amplified detected rod material volumetric segment transmitted beam output signals sent from transmitted beam signal first and second amplifiers 94 and 96, respectively, for forming a detection unit signal integrator output signal. In the first specific configuration of detection unit 40 in electro-optical transmission module 24 of electro-optical inspection device 10, 'without inclusion' of at least one strategically located detection unit temperature sensor, $TS_d$, 100 and an operatively coupled detection unit signal comparator 104 as part of a temperature change monitoring and compensating electro-optical sub-circuit, detection unit signal integrator output signal is directly sent to detection unit output signal buffer 106.

Detection unit output signal buffer 106, in the first specific configuration of detection unit 40 in electro-optical transmission module 24 of electro-optical inspection device 10, is for directly receiving the detection unit signal integrator output signal sent from detection unit signal integrator 98, and storing the detection unit signal integrator output signal in the form of a stored detection unit output signal 106'. Stored detection unit output signal 106' is sent to a process control and data analysis unit, for example, process control and data analysis unit 120, as shown in FIG. 1, for determining the internal properties and characteristics, such as density, structure, defects, and impurities, and variabilities thereof, of longitudinally moving rod of material 12. The determined internal properties and characteristics of moving rod of material 12 are useable by a process control and data analysis unit, for example, process control and data analysis unit 120, for controlling the process of electro-optically inspecting moving rod of material 12, and/or for controlling downstream processing of longitudinally moving rod of material 12.

Detection unit component connections and linkages 108 in the first specific configuration of detection unit 40 in electro-optical transmission module 24 of electro-optical inspection device 10, are for operatively connecting and linking the components, in particular, (1) transmitted beam first detector 90, (2) transmitted beam second detector 92, (3) transmitted beam signal first amplifier 94, (4) transmitted beam signal second amplifier 96, (5) detection unit signal integrator 98, and (6) detection unit signal buffer 106, which are included in the first specific configuration of detection unit 40.

While electro-optically inspecting longitudinally moving rod of material 12, temperature changes typically occur in critical regions of operation of detection unit 40 in electro-optical transmission module 24 of electro-optical inspection device 10, particularly in the immediate vicinity of the electro-optically inspected volumetric segment 34 of moving rod of material 12. Magnitudes of such temperature changes may be sufficiently large so as to significantly increase noise and error levels during the detection (data collection and measurement) process, which may translate to meaningful decreases in accuracy and precision of the results obtained from the electro-optical inspection process.

For achieving higher sensitivity, signal to noise ratios, accuracy, and precision, and therefore, overall performance, of detection unit 40 for detecting rod material volumetric segment transmitted beam 38 of electromagnetic radiation, in electro-optical transmission module 24 of electro-optical inspection device 10, preferably, detection unit 40 further includes components, in particular, at least one strategically located detection unit temperature sensor, $TS_d$, 100 and an operatively coupled detection unit signal comparator 104, and associated electro-optical circuitry, and, sub-steps and procedures, implemented via corresponding algorithms and software programs, for operating thereof, for monitoring temperature and compensating for temperature changes in critical regions of operation of detection unit 26 in electro-optical transmission module 24 of electro-optical inspection device 10. Such critical regions of operation are particularly in the immediate vicinity of the electro-optically inspected volumetric segment 34 of rod of material 12 longitudinally moving along optical path 20 within transparent passageway 22, during the electro-optical inspection process.

Accordingly, in a second specific, more preferred, configuration of detection unit 40 in electro-optical transmission module 24 of electro-optical inspection device 10, detection unit 40 includes the main components: (1) transmitted beam first detector 90, (2) transmitted beam second detector 92, (3) transmitted beam signal first amplifier 94, (4) transmitted beam signal second amplifier 96, (5) detection unit signal integrator 98, (6) detection unit signal buffer 106, and (7) detection unit component connections and linkages 108, and further includes additional main components: (8) a detection unit temperature sensor, $TS_d$, 100, (9) a detection unit temperature sensor signal amplifier 102, and (10) a detection unit signal comparator 104.

Detection unit signal integrator 98, as in the preceding description of the first specific configuration of detection unit 40, is for receiving, and integrating the values of, the corresponding amplified detected rod material volumetric segment transmitted beam output signals sent from transmitted beam signal first and second amplifiers 94 and 96, respectively, for forming a detection unit signal integrator output signal. In the second specific configuration of detection unit 40 in electro-optical transmission module 24 of electro-optical inspection device 10, with inclusion of at least one strategically located detection unit temperature sensor, $TS_d$, 100 and an operatively coupled detection unit signal comparator 104 as part of a temperature change monitoring and compensating electro-optical sub-circuit, detection unit signal integrator output signal is sent to detection unit signal comparator 104.

Detection unit temperature sensor, $TS_d$, 100, is for monitoring and sensing the temperature, typically, in the range of between about 50° C. and 60° C., in the critical region of operation of detection unit 40. As shown in FIG. 1, such critical region of operation is particularly in the immediate vicinity of the electro-optically inspected volumetric segment 34 of rod of material 12 longitudinally moving along optical path 20 within transparent passageway 22, during the electro-optical inspection process. More specifically, the critical region of operation is in the immediate vicinity where rod material volumetric segment transmitted beam 38 is transmitted from volumetric segment 34 and then transmitted through second side 36 of transparent passageway 22, and then detected and received by transmitted beam first and second detectors 90 and 92, for forming detected rod material volumetric segment transmitted beam 38'.

Detection unit temperature sensor, $TS_d$, 100, generates a detection unit temperature sensor output signal proportional to the sensed temperature in the critical region of operation of detection unit 40, and sends the detection unit temperature sensor output signal to detection unit temperature sensor signal amplifier 102. In general, detection unit temperature sensor, $TS_d$, 100, is any appropriately compact or miniature sized and configured temperature sensing device, mechanism, or component, for example, a thermocouple, capable of sensing temperature, and generating an electrical or electronic signal corresponding and proportional to the sensed temperature. For process design, process control, and reference purposes, calibration data and information correlating a range of values of the input sensed temperature with a corresponding range of values of the corresponding detection unit temperature sensor output signal, are empirically determined using standardized conditions of operating electro-optical transmission module 24.

Detection unit temperature sensor signal amplifier 102 is for receiving the detection unit temperature sensor output signal sent from detection unit temperature sensor, $TS_d$, 100, and for amplifying the detection unit temperature sensor output signal. The amplified detection unit temperature sensor output signal is sent to detection unit signal comparator 104.

Detection unit signal comparator 104 is for receiving the amplified detection unit temperature sensor output signal sent from detection unit temperature sensor signal amplifier 102, and for receiving the detection unit signal integrator output signal sent from detection unit signal integrator 98. Detection unit signal comparator 104 then compares, and adds or subtracts, in a temperature compensative manner, the value of the amplified detection unit temperature sensor output signal, to or from, respectively, the value of the detection unit signal integrator output signal, according to the magnitude and the direction or sign (positive or negative) of the temperature change represented by the amplified detection unit temperature sensor output signal, for generating a detection unit signal comparator output signal, herein, also referred to as a detection unit temperature change compensated output signal, which is sent to detection unit output signal buffer 106.

Detection unit output signal buffer 106, in the second specific configuration of detection unit 40 in electro-optical transmission module 24 of electro-optical inspection device 10, receives the detection unit signal comparator output signal (detection unit temperature change compensated output signal) sent from detection unit signal comparator 104, and stores the detection unit signal comparator output signal (detection unit temperature change compensated output signal) in the form of a stored detection unit temperature change compensated output signal 106'. Stored detection unit temperature change compensated output signal 106' is sent to a process control and data analysis unit, for example, process control and data analysis unit 120, as shown in FIG. 1, for determining the internal properties and characteristics, such as density, structure, defects, and impurities, and variabilities thereof, of longitudinally moving rod of material 12. The determined internal properties and characteristics of moving rod of material 12 are useable by a process control and data analysis unit, for example, process control and data analysis unit 120, for controlling the process of electro-optically inspecting moving rod of material 12, and/or for controlling downstream processing of longitudinally moving rod of material 12.

Detection unit component connections and linkages 108 in the second specific configuration of detection unit 40 in electro-optical transmission module 24 of electro-optical inspection device 10, are for operatively connecting and linking the components, in particular, (1) transmitted beam first detector 90, (2) transmitted beam second detector 92, (3) transmitted beam signal first amplifier 94, (4) transmitted beam signal second amplifier 96, (5) detection unit signal integrator 98, (6) detection unit signal buffer 106, and additional components, (8) detection unit temperature sensor, $TS_d$, 100, (9) detection unit temperature sensor signal amplifier 102, and (10) detection unit signal comparator 104, included in the second specific configuration of detection unit 40, in the form of an electro-optical detection circuit which includes monitoring and compensating for temperature changes.

In the second specific configuration of detection unit 40 in electro-optical transmission module 24 of electro-optical inspection device 10, the additional components, (8) detection unit temperature sensor, $TS_d$, 100, (9) detection unit temperature sensor signal amplifier 102, and (10) detection unit signal comparator 104, form a temperature change monitoring and compensating electro-optical detection sub-circuit, based upon, and in accordance with, operation of the strategically located detection unit temperature sensor, $TS_d$, 100 and operatively coupled detection unit signal comparator 104, and associated electro-optical circuitry, included in detection unit 40, involving the detection unit temperature sensor output signal sent by detection unit temperature sensor, $TS_d$, 100, which in turn, is proportional to the sensed temperature in the critical region of operation of detection unit 40. Thus, overall operation of detection unit 40 is based on, and in accordance with, a temperature change monitoring and compensating electro-optical detection circuit.

Automatic operations of detection unit 40, in general, and of the above described electrical and electronic components and elements thereof, in electro-optical transmission module 24 of electro-optical inspection device 10, are performed by a process control and data analysis unit, such as process control and data analysis unit 120.

In FIG. 1, with reference to reference XYZ coordinate system 50, it is shown that electro-optical inspection device 10, in general, including illumination unit 26, detection unit 40, and preferably, a module housing 42 of selected components of these units, of electro-optical transmission module 24, in particular, are geometrically configured, positioned, and operative, such that electromagnetic radiation source beam 44 generated by illumination unit 26 is focused, via focusing lens 46, for example, in the negative Y-direction towards first side 30 (perspectively viewed and understood as towards the top side) of transparent passageway 22 and is also incident, via polarizing beam splitter 48, for example, in the negative Y-direction upon rod of material 12 longitudinally moving in the positive Z-direction along coaxial optical path 20 within transparent passageway 22.

Accordingly, incident focused beam 32 illuminates, in the negative Y-direction, volumetric segment 34 of longitudinally moving rod of material 12, such that at least part of incident focused beam 32 is affected by and transmitted in the negative Y-direction through volumetric segment 34, and then transmitted in the negative Y-direction through second side 36 (perspectively viewed and understood as through the bottom side) of transparent passageway 22, for forming rod material volumetric segment transmitted beam 38. Rod material volumetric segment transmitted beam 38 is detected by detection unit 40, for forming detected rod material volumetric segment transmitted beam 38' useable for determining the internal properties and characteristics of the longitudinally moving rod of material 12.

Following are illustratively described the steps and substeps of the generalized method, and the components, elements, operation, and implementation, of the generalized electro-optical inspection device, of the present invention, with reference to the second exemplary specific preferred embodiment of the generalized electro-optical inspection device, electro-optical inspection device 60, of the present invention, as illustrated in FIG. 2.

In Step (a), there is guiding the longitudinally moving rod of material along its longitudinal axis by a rod guiding unit, along an optical path within a transparent passageway, the optical path and the transparent passageway coaxially extend along the longitudinal axis of the moving rod of material and pass through an electro-optical transmission module.

In the second exemplary specific preferred embodiment of the generalized device for electro-optically inspecting and determining internal properties and characteristics of a longitudinally moving rod of material, that is, moving rod of material 12, as illustrated in FIG. 2, electro-optical inspection device 60 includes the main components: (a) a rod guiding unit 14, and (b) a plurality of two electro-optical transmission modules 24a and 24b.

In electro-optical inspection device 60, rod guiding unit 14 guides moving rod of material 12 along its longitudinal axis, extending between rod material entrance area 16 and rod material exit area 18 of electro-optical inspection device 60, along an optical path 20 (in FIG. 2, indicated by the dotted line 20 drawn along the length of moving rod of material 12) within a transparent passageway 22, where optical path 20 and transparent passageway 22 coaxially extend along the longitudinal axis of moving rod of material 12. Preferably, rod guiding unit 14 is operatively connected to a rod moving unit, such as rod moving unit 5, for example, via rod material entrance area 16, for receiving longitudinally moving rod of material 12 provided and supplied by rod moving unit 5.

Rod guiding unit 14 includes the main components: (i) a transparent housing 62, and (ii) a rod material entrance assembly 64.

Transparent housing 62 houses, holds, or confines, transparent passageway 22 within which is coaxial optical path 20, along which is guided longitudinally moving rod of material 12. Transparent housing 62 is, preferably, of a hollow tubular or cylindrical geometrical shape, and constructed from an optically transparent material, for example, a plastic, a glass, a transparent composite material, or a combination thereof.

Rod material entrance assembly 64 is operatively attached or connected to transparent housing 62, and functions as an entrance for the longitudinally moving rod of material 12 entering into electro-optical inspection device 10, via rod material entrance area 16. Preferably, rod material entrance assembly 64 is operatively connected to a rod moving unit, such as rod moving unit 5, thereby enabling operative connection of rod guiding unit 14 with rod moving unit 5. Rod material entrance assembly 64 is preferably of a mostly hollow tubular or cylindrical geometrical shape, and constructed from a metallic material, a non-metallic material, a composite material, or a combination thereof, for enabling operative attachment or connection to transparent housing 62 and for enabling guiding of the moving rod of material 12 along its longitudinal axis along optical path 20 within coaxial transparent passageway 22.

For proper implementation of the electro-optical inspection method and electro-optical inspection device 60, the optically transparent material of transparent housing 62 in rod guiding unit 14 is compatible with the properties, characteristics, and operation, of each illumination unit 26a and 26b. Especially, regarding wavelength or frequency, and intensity or power, of electromagnetic radiation source beams 44a and 44b generated by illumination units 26a and 26b, respectively, such that focused beams 28a and 28b, respectively, are transmittable through first sides 30a and 30b, respectively, of transparent passageway 22 and subsequently incident upon volumetric segments 34a and 34b, respectively, of rod of material 12 longitudinally moving within transparent passageway 22.

Moreover, this compatibility is such that subsequent to incident focused beams 32a and 32b, respectively, illuminating volumetric segments 34a and 34b, respectively, of moving rod of material 12, and subsequent to at least part of incident focused beams 32a and 32b, respectively, being affected by and transmitted through volumetric segments 34a and 34b, respectively, the affected incident focused beam exiting volumetric segments 34a and 34b, respectively, is then transmittable through second sides 36a and 36b, respectively, of transparent passageway 22, for forming rod material volumetric segment transmitted beams 38a and 38b, respectively. This in turn, enables detection of rod material volumetric segment transmitted beams 38a and 38b, respectively, for forming detected rod material volumetric segment transmitted beams 38'a and 38'b, respectively, useable for determining the internal properties and characteristics of the longitudinally moving rod of material 12.

In Step (b), there is generating a focused beam of electromagnetic radiation by an illumination unit of the electro-optical transmission module, such that the focused beam is transmitted through a first side of the transparent passageway and incident upon the rod of material longitudinally moving within the transparent passageway. In Step (c), there is illuminating a volumetric segment of the longitudinally moving rod of material by the incident focused beam, such that at least part of the incident focused beam is affected by and transmitted through the volumetric segment and then transmitted through a second side of the transparent passageway, for forming a rod material volumetric segment transmitted beam.

In electro-optical inspection device 60, as illustrated in FIG. 2, each electro-optical transmission module 24a and 24b through which pass optical path 20 and transparent passageway 22, includes the main components: (i) an illumination unit 26a and 26b, respectively, and (ii) a detection unit 40a and 40b, respectively.

Each illumination unit 26a and 26b, respectively, generates a focused beam 28a and 28b, respectively, of electromagnetic radiation, such that focused beam 28a and 28b, respectively, is transmitted through a first side 30a and 30b, respectively, of transparent passageway 22 and incident upon rod of material 12 longitudinally moving within transparent passageway 22, and the incident focused beam 32a and 32b, respectively, illuminates a volumetric segment 34a and 34b, respectively, of longitudinally moving rod of material 12, such that at least part of incident focused beam 32a and 32b, respectively, is affected by and transmitted through volumetric segment 34a and 34b, respectively, and then transmitted through a second side 36a and 36b, respectively, of transparent passageway 22, for forming a rod material volumetric segment transmitted beam 38a and 38b, respectively.

In a first specific configuration of each illumination unit 26a and 26b in electro-optical transmission module 24a and 24b, respectively, of electro-optical inspection device 60, each illumination unit 26a and 26b, respectively, includes the main components: (1) an electromagnetic radiation beam source 70a and 70b, respectively, and (2) a focusing lens 46a and 46b, respectively.

In the first specific configuration of each illumination unit 26a and 26b in electro-optical transmission module 24a and 24b, respectively, of electro-optical inspection device 60, each illumination unit 26a and 26b, respectively, 'does not include' components, in particular, a polarizing beam splitter 48a and 48b, respectively, at least one strategically located operatively coupled optical feedback reference beam detector 74a and 74b, respectively, and illumination unit temperature sensor, $TS_i$, 78a and 78b, respectively, and associated electro-optical feedback circuitry, and, sub-steps and procedures, implemented via corresponding algorithms and software programs, for operating thereof, for monitoring temperature and compensating for temperature changes in critical regions of operation of illumination unit 26a and 26b in electro-optical transmission module 24a and 24b, respectively, of electro-optical inspection device 60.

Each electromagnetic radiation beam source 70a and 70b, respectively, generates and emits an electromagnetic radiation source beam 44a and 44b, respectively. Electromagnetic radiation beam source 70a and 70b, respectively, is any appropriately compact or miniature sized and configured device, mechanism, or component, capable of generating and emitting an electromagnetic radiation source beam 44a and 44b, respectively. Electromagnetic radiation beam source 70a and 70b, respectively, is of structure and functions according to either light emitting diode (LED) technology, or fiber optic technology. For example, electromagnetic radiation beam source 70a and 70b, respectively, is a light emitting diode (LED). Alternatively, electromagnetic radiation beam source 70a and 70b, respectively, is an operative combination, for example, an integral device, of an electromagnetic radiation beam generator, for example, a lamp or a laser, and a fiber optic conductor or fiber optic guide.

In general, electromagnetic radiation source beam 44a and 44b, respectively, generated and emitted by electromagnetic radiation beam source 70a and 70b, respectively, is infrared radiation, visible light, or ultraviolet radiation. Preferably, for electro-optically inspecting and determining internal properties and characteristics, such as density, structure, defects, and impurities, and variabilities thereof, of a volumetric segment 34a and 34b, respectively, of moving rod of material 12 being a cigarette rod, consisting of processed tobacco inside a rolled and sealed tube of cigarette wrapping paper, electromagnetic radiation source beam 44a and 44b, respectively, is infrared radiation having wavelength in the range of between about 900 nm and about 1000 nm, and more preferably, having wavelength in the range of between about 920 nm and about 970 nm.

Each focusing lens 46a and 46b, respectively, focuses electromagnetic radiation source beam 44a and 44b, respectively, for forming focused beam 28a and 28b, respectively. In the first specific configuration of illumination unit 26a and 26b in electro-optical transmission module 24a and 24b, respectively, of electro-optical inspection device 60, 'without inclusion' of a polarizing beam splitter 48a and 48b and other components of a temperature change monitoring and compensating electro-optical feedback loop in each illumination unit 26a and 26b, respectively, focused beam 28a and 28b, respectively, becomes incident focused beam 32a and 32b, respectively, which is transmitted through first side 30a and 30b, respectively, of transparent passageway 22 and incident upon volumetric segment 34a and 34b, respectively.

Incident focused beam 32a and 32b, respectively, illuminates volumetric segment 34a and 34b, respectively, of rod of material 12 longitudinally moving along coaxial optical path 20 within transparent passageway 22, such that at least part of incident focused beam 32a and 32b, respectively, is affected by and transmitted through volumetric segment 34a and 34b, respectively, and then transmitted through second side 36a and 36b, respectively, of transparent passageway 22, for forming rod material volumetric segment transmitted beam 38a and 38b, respectively. Rod material volumetric segment transmitted beam 38a and 38b, respectively, is detected by a detection unit 40a and 40b, respectively, in electro-optical transmission module 24a and 24b, respectively, of electro-optical inspection device 60, for forming a detected rod material volumetric segment transmitted beam 38'a and 38'b, respectively, useable for determining the internal properties and characteristics of the longitudinally moving rod of material 12, as described in further detail below.

While electro-optically inspecting longitudinally moving rod of material 12, temperature changes typically occur in critical regions of operation of each illumination unit 26a and 26b in electro-optical transmission module 24a and 24b, respectively, of electro-optical inspection device 60, particularly in the immediate vicinity of each electro-optically inspected volumetric segment 34a and 34b of moving rod of material 12. Magnitudes of such temperature changes may be sufficiently large so as to significantly increase noise and error levels during the illumination process, which may translate to meaningful decreases in accuracy and precision of the results obtained from the electro-optical inspection process.

For achieving higher sensitivity, signal to noise ratios, accuracy, and precision, and therefore, overall performance, of each illumination unit 26a and 26b, for generating focused beam 28a and 28b, respectively, and incident focused beam 32a and 32b, respectively, of electromagnetic radiation, in each electro-optical transmission module 24a and 24b of electro-optical inspection device 60, preferably, each illumination unit 26a and 26b further includes components, in particular, a polarizing beam splitter 48a and 48b, respectively, at least one strategically located operatively coupled optical feedback reference beam detector 74a and 74b, respectively, and illumination unit temperature sensor, $TS_i$, 78a and 78b, respectively, and associated electro-optical feedback circuitry, and, sub-steps and procedures, implemented via corresponding algorithms and software programs, for operating thereof, for monitoring temperature and compensating for temperature changes in critical regions of operation of each illumination unit 26a and 26b of each electro-optical transmission module 24a and 24b, respectively, of electro-optical inspection device 60. Such critical regions of operation are particularly in the immediate vicinity of each electro-optically inspected volumetric segment 34a and 34b, respectively, of rod of material 12 longitudinally moving along optical path 20 within transparent passageway 22, during the electro-optical inspection process.

Accordingly, in a second specific, more preferred, configuration of each illumination unit 26a and 26b in electro-optical transmission module 24a and 24b, respectively, of electro-optical inspection device 60, each illumination unit 26a and 26b includes the main components: (1) electromagnetic radiation beam source 70a and 70b, respectively, and (2) focusing lens 46a and 46b, respectively, and further includes additional main components: (3) a polarizing beam splitter 48a and 48b, respectively, (4) an optical feedback reference beam detector 74a and 74b, respectively, (5) an optical feedback reference beam signal amplifier 76a and 76b, respectively, (6) an illumination unit temperature sensor, $TS_i$, 78a and 78b, respectively, (7) an illumination unit temperature sensor signal amplifier 80a and 80b, respectively, (8) an illumination unit signal comparator 82a and 82b, respectively, (9) a proportional integrated (PI) regulator 84a and 84b, respectively, (10) a current regulator 86a and 86b, respectively, and (11) illumination unit electro-optical feedback loop component connections and linkages 88a and 88b, respectively.

Focusing lens 46a and 46b, respectively, as in the preceding description of the first specific configuration of illumination unit 26a and 26b, respectively, focuses electromagnetic radiation source beam 44a and 44b, respectively, for forming focused beam 28a and 28b, respectively. In the second specific configuration of illumination unit 26a and 26b in electro-optical transmission module 24a and 24b, respectively, of electro-optical inspection device 60, with inclusion of a polarizing beam splitter 48a and 48b and the other components, (4)-(11), of a temperature change monitoring and compensating electro-optical feedback loop in each illumination unit 26a and 26b, respectively, focused beam 28a and 28b propagates into polarizing beam splitter 48a and 48b, respectively.

Polarizing beam splitter 48a and 48b, respectively, splits focused beam 28a and 28b, respectively, into two separate beams, an optical feedback reference beam 72a and 72b, respectively, and incident focused beam 32a and 32b, respectively. Optical feedback reference beam 72a and 72b, respectively, is fed back into the electro-optical circuit of illumination unit 26a and 26b, respectively, via optical feedback reference beam detector 74a and 74b, respectively, while incident focused beam 32a and 32b, respectively, is transmitted through first side 30a and 30b, respectively, of transparent passageway 22 and incident upon volumetric segment 34a and 34b, respectively, thereby illuminating volumetric segment 34a and 34b, respectively, of rod of material 12 longitudinally moving along coaxial optical path 20 within transparent passageway 22.

In general, the area of illumination, or illuminating area, of incident focused beam 32a and 32b, respectively, directly originating from focused beam 28a and 28b, respectively, without first passing through polarizing beam splitter 48a and 48b, respectively (in accordance with the first specific configuration of illumination unit 26a and 26b, respectively), or originating from focused beam 28a and 28b, respectively, after first passing through polarizing beam splitter 48a and 48b, respectively (in accordance with the second specific configuration of illumination unit 26a and 26b, respectively), is of a variable magnitude, and is selected and used in accordance with the magnitude of the outer or external circumferential area of moving rod of material 12, and in accordance with the magnitude of the average or characteristic diameter of the smallest particles or substances making up rod of material 12, which are of analytical interest and inspected during the electro-optical inspection process. The area of illumination, or illuminating area, of incident focused beam 32a and 32b, respectively, corresponds to the initial or frontal area of moving rod of material 12 upon which incident focused beam 32a and 32b, respectively, is incident.

In FIG. 2, with reference to reference XYZ coordinate system 50, it is shown that during operation of electro-optical inspection device 60, electromagnetic radiation source beam 44a generated by illumination unit 26a is focused, via focusing lens 46a, in the negative Y-direction towards first side 30a (in FIG. 2, to be perspectively viewed and understood as from above and towards the top side) of transparent passageway 22 and is also incident, via polarizing beam splitter 48a, in the negative Y-direction upon rod of material 12 longitudinally moving in the positive Z-direction along coaxial optical path 20 within transparent passageway 22. Incident focused beam 32a illuminates, in the negative Y-direction, volumetric segment 34a of longitudinally moving rod of material 12. Accordingly, the area of illumination, or illuminating area, of incident focused beam 32a corresponds to the 'initial or frontal' area (in FIG. 2, to be perspectively viewed and understood as the top side area) of volumetric segment 34a upon which incident focused beam 32a is incident.

In a similar manner, in FIG. 2, it is shown that during operation of electro-optical inspection device 60, electromagnetic radiation source beam 44b generated by illumination unit 26b is focused, via focusing lens 46b, in the positive X-direction towards first side 30b (in FIG. 2, to be perspectively viewed and understood as from behind and towards the back side) of transparent passageway 22 and is also incident, via polarizing beam splitter 48b, in the positive X-direction upon rod of material 12 longitudinally moving in the positive Z-direction along coaxial optical path 20 within transparent passageway 22. Incident focused beam 32b illuminates, in the positive X-direction, volumetric segment 34b of longitudinally moving rod of material 12. Accordingly, the area of illumination, or illuminating area, of incident focused beam 32b corresponds to the initial or frontal area (in FIG. 1, to be perspectively viewed and understood as the back side area) of volumetric segment 34b upon which incident focused beam 32b is incident.

Preferably, the magnitude of the area of illumination, or illuminating area, of incident focused beam 32a and 32b, respectively, is less than the magnitude of the outer or external circumferential area of moving rod of material 12, and greater than the magnitude of the average or characteristic diameter of the smallest particles or substances making up rod of material 12, which are of analytical interest and inspected during the electro-optical inspection process. For example, preferably, for electro-optically inspecting and determining internal properties and characteristics of volumetric segments 34a and 34b, respectively, of moving rod of material 12 being a cigarette rod, the magnitude of the area of illumination, or illuminating area, of incident focused beam 32a and 32b, respectively, is less than the magnitude, typically, on the order of about 1 cm, of the outer or external circumferential area of the cigarette rod, and greater than the magnitude of the average or characteristic diameter, typically, on the order of about 4 mm, of the smallest particles or substances making up the cigarette rod, which are of analytical interest and inspected during the electro-optical inspection process.

Optical feedback reference beam detector 74a and 74b, respectively, detects and receives optical feedback reference beam 72a and 72b, respectively, output from polarizing beam splitter 48a and 48b, respectively, and converts optical feedback reference beam 72a and 72b, respectively, into a corresponding optical feedback reference beam output signal, which is sent back into the electro-optical circuit of illumination unit 26a and 26b, respectively, via optical feedback reference beam signal amplifier 76a and 76b, respectively.

Each optical feedback reference beam detector 74a and 74b is any appropriately compact or miniature sized and configured device, mechanism, or component, capable of detecting and receiving electromagnetic radiation source beam 44a and 44b, respectively, generated and emitted according to either light emitting diode (LED) technology, or fiber optic technology, and for converting such a detected and received beam into a corresponding output signal. For example, each optical feedback reference beam detector 74a and 74b is of structure and functions as a light receiving type of device, mechanism, component, or element, such as a phototransistor, a photosensitive transducer, a fiber optic conductor or guide, or a photoelectric element. For process design, process control, and reference purposes, calibration data and information correlating a range of values of the input optical feedback reference beam 72a and 72b, respectively, with a range of values of the corresponding optical feedback reference beam output signal, are empirically determined using standardized conditions of operating electro-optical transmission module 24a and 24b.

Optical feedback reference beam signal amplifier 76a and 76b, respectively, receives the optical feedback reference beam output signal sent from optical feedback reference beam detector 74a and 74b, respectively, and amplifies the optical feedback reference beam signal. The amplified optical feedback reference beam signal is then sent to illumination unit signal comparator 82a and 82b, respectively.

Illumination unit temperature sensor, $TS_i$, 78a and 78b, respectively, monitors and senses the temperature, typically, in the range of between about 50° C. and 60° C., in the critical region of operation of illumination unit 26a and 26b, respectively. As shown in FIG. 2, such critical region of operation is particularly in the immediate vicinity of the electro-optically inspected volumetric segment 34a and 34b, respectively, of rod of material 12 longitudinally moving along optical path 20 within transparent passageway 22, during the electro-optical inspection process. More specifically, the critical region of operation is in the immediate vicinity where incident focused beam 32a and 32b, respectively, is transmitted through first side 30a and 30b, respectively, of transparent passageway 22 and incident upon volumetric segment 34a and 34b, respectively, for illuminating volumetric segment 34a and 34b, respectively, of rod of material 12 longitudinally moving along coaxial optical path 20 within transparent passageway 22.

Illumination unit temperature sensor, $TS_i$, 78a and 78b, respectively, generates an illumination unit temperature sensor output signal proportional to the sensed temperature in the critical region of operation of illumination unit 26a and 26b, respectively, and sends the illumination unit temperature sensor output signal back into the electro-optical circuit, herein, also referred to as the electro-optical feedback loop, of illumination unit 26a and 26b, respectively, via illumination unit temperature sensor signal amplifier 80a and 80b, respectively. In general, illumination unit temperature sensor, $TS_i$, 78a and 78b, respectively, is any appropriately compact or miniature sized and configured temperature sensing device, mechanism, or component, for example, a thermocouple, capable of sensing temperature, and generating an electrical or electronic signal corresponding and proportional to the sensed temperature. For process design, process control, and reference purposes, calibration data and information correlating a range of values of the input sensed temperature with a range of values of the corresponding illumination unit temperature sensor output signal, are empirically determined using standardized conditions of operating electro-optical transmission modules 24a and 24b.

Illumination unit temperature sensor signal amplifier 80a and 80b, respectively, receives the illumination unit temperature sensor output signal sent from illumination unit temperature sensor, $TS_i$, 78a and 78b, respectively, and then amplifies the illumination unit temperature sensor output signal. The amplified illumination unit temperature sensor output signal is then sent to illumination unit signal comparator 82a and 82b, respectively.

Illumination unit signal comparator 82a and 82b, respectively, receives the amplified optical feedback reference beam output signal sent from optical feedback reference beam signal amplifier 76a and 76b, respectively, and receives the amplified illumination unit temperature sensor output signal sent from illumination unit temperature sensor signal amplifier 80a and 80b, respectively. Illumination unit signal comparator 82a and 82b, respectively, then compares, and adds or subtracts, in a compensative manner, the value of the amplified illumination unit temperature sensor output signal, to or from, respectively, the value of the amplified optical feedback reference beam output signal, according to the magnitude and the direction or sign (positive or negative) of the temperature change represented by the amplified illumination unit temperature sensor output signal, for generating an illumination unit signal comparator output signal, which is sent to proportional integrated (PI) regulator 84a and 84b, respectively.

Proportional integrated (PI) regulator 84a and 84b, respectively, receives the illumination unit signal comparator output signal sent from illumination unit signal comparator 82a and 82b, respectively, and generates a proportional integrated (PI) regulator output signal, which is sent to current regulator 86a and 86b, respectively.

Current regulator 86a and 86b, respectively, receives the proportional integrated (PI) regulator output signal sent from proportional integrated (PI) regulator 84a and 84b, respectively, and generates a current regulator output signal, which is sent to electromagnetic radiation beam source 70a and 70b, respectively. In proportion to the magnitude of the proportional integrated (PI) regulator output signal, the current regulator output signal regulates, in a temperature compensative manner, the level of current used by electromagnetic radiation beam source 70a and 70b, respectively, and therefore, regulates, in a temperature compensative manner, the generation and emission, via regulating wavelength or frequency, and intensity or power, of electromagnetic radiation source beam 44a and 44b, respectively, by electromagnetic radiation beam source 70a and 70b, respectively. For process design, process control, and reference purposes, calibration data and information correlating a range of values of the input proportional integrated (PI) regulator signal with a corresponding range of values of the corresponding current regulator output signal, are empirically determined using standardized conditions of operating electro-optical transmission modules 24a and 24b.

Illumination unit electro-optical feedback loop component connections and linkages 88a and 88b, respectively, operatively connect and link the components, in particular, (1) electromagnetic radiation beam source 70a and 70b, respectively, (4) optical feedback reference beam detector 74a and 74b, respectively, (5) optical feedback reference beam signal amplifier 76a and 76b, respectively, (6) illumination unit temperature sensor, $TS_i$, 78a and 78b, respectively, (7) illumination unit temperature sensor signal amplifier 80a and 80b, respectively, (8) illumination unit signal comparator 82a and 82b, respectively, (9) proportional integrated (PI) regulator 84a and 84b, respectively, and (10) current regulator 86a and 86b, respectively, included in the second specific configuration of illumination unit 26a and 26b, respectively, in electro-optical transmission module 24a and 24b, respectively, of electro-optical inspection device 60, in the form of an electro-optical feedback loop, based on monitoring and compensating for temperature changes.

In the second specific configuration of illumination unit 26a and 26b, respectively, in electro-optical transmission module 24a and 24b, respectively, of electro-optical inspection device 60, the regulatory, temperature compensative, action performed by each proportional integrated (PI) regulator 84a and 84b and current regulator 86a and 86b, respectively, is based upon, and in accordance with, operation of the strategically located operatively coupled optical feedback reference beam detector 74a and 74b, respectively, and temperature sensor, $TS_i$, 78a and 78b, respectively, and associated electro-optical feedback circuitry, included in illumination unit 26a and 26b, respectively, involving the illumination unit temperature sensor output signal sent by illumination unit temperature sensor 78a and 78b, respectively, which in turn, is proportional to the sensed temperature in the critical region of operation of illumination unit 26a and 26b, respectively. Thus, overall operation of each illumination unit 26a and 26b is based on, and in accordance with, a temperature change monitoring and compensating electro-optical feedback loop.

Automatic operations of each illumination unit 26a and 26b, in general, and of the above described electrical and electronic components and elements thereof, in each electro-optical transmission module 24a and 26b, respectively, of electro-optical inspection device 60, are performed by a process control and data analysis unit, such as process control and data analysis unit 120.

In Step (d), there is detecting the rod material volumetric segment transmitted beam by a detection unit of the electro-optical transmission module, for forming a detected rod material volumetric segment transmitted beam useable for determining the internal properties and characteristics of the longitudinally moving rod of material.

As described above, according to operation of either the first or second specific configuration of illumination units 26a and 26b in electro-optical transmission module 24a and 24b, respectively, of electro-optical inspection device 60, incident focused beam 32a and 32b, respectively, illuminates volumetric segment 34a and 34b, respectively, of longitudinally moving rod of material 12, such that at least part of incident focused beam 32a and 32b, respectively, is affected by and transmitted through volumetric segment 34a and 34b, respectively, and then transmitted through second side 36a and 36b, respectively, of transparent passageway 22, for forming rod material volumetric segment transmitted beam 38a and 38b, respectively. In each electro-optical transmission module 24a and 24b, respectively, of electro-optical inspection device 60, detection unit 40a and 40b, respectively, detects rod material volumetric segment transmitted beam 38a and 38b, respectively, and forms a detected rod material volumetric segment transmitted beam 38'a and 38'b, respectively, useable for determining the internal properties and characteristics of the longitudinally moving rod of material 12.

In a first specific configuration of each detection unit 40a and 40b in electro-optical transmission module 24a and 24b, respectively, of electro-optical inspection device 60, each detection unit 40a and 40b, respectively, includes the main components: (1) a transmitted beam first detector 90a and 90b, respectively, (2) a transmitted beam second detector 92a and 92b, respectively, (3) a transmitted beam signal first amplifier 94a and 94b, respectively, (4) a transmitted beam signal second amplifier 96a and 96b, respectively, (5) a detection unit signal integrator 98a and 98b, respectively, (6) a detection unit signal buffer 106a and 106b, respectively, and (7) detection unit component connections and linkages 108a and 108b, respectively.

In the first specific configuration of each detection unit 40a and 40b in electro-optical transmission module 24a and 24b, respectively, of electro-optical inspection device 60, each detection unit 40a and 40b, respectively, 'does not include' components, in particular, at least one strategically located detection unit temperature sensor, $TS_d$, 100a and 100b, respectively, and an operatively coupled detection unit signal comparator 104a and 104b, respectively, and associated electro-optical circuitry, and, sub-steps and procedures, implemented via corresponding algorithms and software programs, for operating thereof, for monitoring temperature and compensating for temperature changes in critical regions of operation of each detection unit 40a and 40b, respectively, in electro-optical transmission module 24a and 24b, respectively, of electro-optical inspection device 60.

Transmitted beam first detector 90a and 90b, respectively, and transmitted beam second detector 92a and 92b, respectively, detect and receive rod material volumetric segment transmitted beam 38a and 38b, respectively, which is transmitted from volumetric segment 34a and 34b, respectively, and then transmitted through second side 36a and 36b, respectively, of transparent passageway 22, for forming detected rod material volumetric segment transmitted beam 38'a and 38'b, respectively. Transmitted beam first detectors 90a and 90b, respectively, and transmitted beam second detectors, 92a and 92b, respectively, each convert part of detected rod material volumetric segment transmitted beam 38'a and 38b', respectively, into a corresponding detected rod material volumetric segment transmitted beam output signal, which is sent to transmitted beam signal first amplifiers 94a and 94b, respectively, and transmitted beam signal second amplifiers 96a and 96b, respectively.

Each transmitted beam first detector 90a and 90b, respectively, and transmitted beam second detector 92a and 92b, respectively, is any appropriately compact or miniature sized and configured device, mechanism, or component, capable of detecting and receiving rod material volumetric segment transmitted beam 38a and 38b, respectively, and for converting such a detected and received beam into a corresponding output signal. For example, each of transmitted beam first 90a and 90b, respectively, and transmitted beam second detector 92a and 92b, respectively, is of structure and functions as a light receiving type of device, mechanism, component, or element, such as a phototransistor, a photosensitive transducer, a fiber optic conductor or guide, or a photoelectric element. For process design, process control, and reference purposes, calibration data and information correlating a range of values of the input rod material volumetric segment transmitted beam 38a and 38b, respectively, with a range of values of the corresponding detected rod material volumetric segment transmitted beam output signals, are empirically determined using standardized conditions of operating electro-optical transmission module 24a and 24b, respectively.

Transmitted beam signal first amplifier 94a and 94b, respectively, and transmitted beam signal second amplifier 96a and 96b, respectively, each receive a corresponding detected rod material volumetric segment transmitted beam output signal, sent from transmitted beam first and second detectors 90a and 90b, and, 92a and 92b, respectively, and then amplify the corresponding detected rod material volumetric segment transmitted beam output signal. The corresponding amplified detected rod material volumetric segment transmitted beam output signals are then sent to detection unit signal integrators 98a and 98b, respectively.

Detection unit signal integrator 98a and 98b, respectively, receives, and integrates the values of, the corresponding amplified detected rod material volumetric segment transmitted beam output signals sent from transmitted beam signal first and second amplifiers 94a and 94b, and, 96a and 96b, respectively, for forming a detection unit signal integrator output signal. In the first specific configuration of each detection unit 40a and 40b in electro-optical transmission module 24a and 24b, respectively, of electro-optical inspection device 60, 'without inclusion' of at least one strategically located detection unit temperature sensor, $TS_d$, 100a and 100b, respectively, and an operatively coupled detection unit signal comparator 104a and 104b, respectively, as part of a temperature change monitoring and compensating electro-optical sub-circuit, detection unit signal integrator output signal is directly sent to detection unit output signal buffer 106a and 106b, respectively.

Detection unit output signal buffer 106a and 106b in the first specific configuration of each detection unit 40a and 40b, respectively, in electro-optical transmission module 24a and 24b, respectively, of electro-optical inspection device 60, directly receives the detection unit signal integrator output signal sent from detection unit signal integrator 98a and 98b, respectively, and stores the detection unit signal integrator output signal in the form of a stored detection unit output signal 106'a and 106'b, respectively. Stored detection unit output signal 106'a and 106'b, respectively, is sent to a process control and data analysis unit, for example, process control and data analysis unit 120, as shown in FIG. 2, for determining the internal properties and characteristics, such as density, structure, defects, and impurities, and variabilities thereof, of longitudinally moving rod of material 12. The determined internal properties and characteristics of moving rod of material 12 are useable by a process control and data analysis unit, for example, process control and data analysis unit 120, for controlling the process of electro-optically inspecting moving rod of material 12, and/or for controlling downstream processing of longitudinally moving rod of material 12.

Detection unit component connections and linkages 108a and 108b, respectively, in the first specific configuration of detection unit 40a and 40b, respectively, in electro-optical transmission module 24a and 24b, respectively, of electro-optical inspection device 60, operatively connect and link the components, in particular, (1) transmitted beam first detector 90a and 90b, respectively, (2) transmitted beam second detector 92a and 92b, respectively, (3) transmitted beam signal first amplifier. 94a and 94b, respectively, (4) transmitted beam signal second amplifier 96a and 96b, respectively, (5) detection unit signal integrator 98a and 98b, respectively, and (6) detection unit signal buffer 106a and 106b, respectively, which are included in the first specific configuration of detection unit 40a and 40b, respectively.

While electro-optically inspecting longitudinally moving rod of material 12, temperature changes typically occur in critical regions of operation of each detection unit 40a and 40b in electro-optical transmission module 24a and 24b, respectively, of electro-optical inspection device 60, particularly in the immediate vicinity of each electro-optically inspected volumetric segment 34a and 34b, respectively, of moving rod of material 12. Magnitudes of such temperature changes may be sufficiently large so as to significantly increase noise and error levels during the detection (data collection and measurement) process, which may translate to meaningful decreases in accuracy and precision of the results obtained from the electro-optical inspection process.

For achieving higher sensitivity, signal to noise ratios, accuracy, and precision, and therefore, overall performance, of each detection unit 40a and 40b for detecting rod material volumetric segment transmitted beam 38a and 38b, respectively, of electromagnetic radiation, in each electro-optical transmission module 24a and 24b of electro-optical inspection device 60, preferably, each detection unit 40a and 40b, respectively, further includes components, in particular, at least one strategically located detection unit temperature sensor, $TS_d$, 100a and 100b, respectively, and an operatively coupled detection unit signal comparator 104a and 104b, respectively, and associated electro-optical circuitry, and, sub-steps and procedures, implemented via corresponding algorithms and software programs, for operating thereof, for monitoring temperature and compensating for temperature changes in critical regions of operation of each detection unit 26a and 26b, respectively, in electro-optical transmission module 24a and 24b, respectively, of electro-optical inspection device 60. Such critical regions of operation are particularly in the immediate vicinity of each electro-optically inspected volumetric segment 34a and 34b, respectively, of rod of material 12 longitudinally moving along optical path 20 within transparent passageway 22, during the electro-optical inspection process.

Accordingly, in a second specific, more preferred, configuration of each detection unit 40a and 40b in electro-optical transmission module 24a and 24b, respectively, of electro-optical inspection device 60, each detection unit 40a and 40b includes the main components: (1) transmitted beam first detector 90a and 98b, respectively, (2) transmitted beam second detector 92a and 92b, respectively, (3) transmitted beam signal first amplifier 94a and 94b, respectively, (4) transmitted beam signal second amplifier 96a and 96b, respectively, (5) detection unit signal integrator 98a and 98b, respectively, (6) detection unit signal buffer 106a and 106b, respectively, and (7) detection unit component connections and linkages 108a and 108b, respectively, and further includes additional main components: (8) a detection unit temperature sensor, $TS_d$, 100a and 100b, respectively, (9) a detection unit temperature sensor signal amplifier 102a and 102b, respectively, and (10) a detection unit signal comparator 104a and 104b, respectively.

Detection unit signal integrator 98a and 98b, respectively, as in the preceding description of the first specific configuration of detection unit 40a and 40b, respectively, receives, and integrates the values of, the corresponding amplified detected rod material volumetric segment transmitted beam output signals sent from transmitted beam signal first and second amplifiers 94a and 94b, and, 96a and 96b, respectively, for forming a detection unit signal integrator output signal. In the second specific configuration of detection unit 40a and 40b, respectively, in electro-optical transmission module 24a and 24b, respectively, of electro-optical inspection device 60, with inclusion of at least one strategically located detection unit temperature sensor, $TS_d$, 100a and 100b, respectively, and an operatively coupled detection unit signal comparator 104a and 104b, respectively, as part of a temperature change monitoring and compensating electro-optical sub-circuit, detection unit signal integrator output signal is sent to detection unit signal comparator 104a and 104b, respectively.

Detection unit temperature sensor, $TS_d$, 100a and 100b, respectively, monitors and senses the temperature, typically, in the range of between about 50° C. and 60° C., in the critical region of operation of each detection unit 40a and 40b, respectively. As shown in FIG. 2, such critical region of operation is particularly in the immediate vicinity of the electro-optically inspected volumetric segment 34a and 34b, respectively, of rod of material 12 longitudinally moving along optical path 20 within transparent passageway 22, during the electro-optical inspection process. More specifically, the critical region of operation is in the immediate vicinity where rod material volumetric segment transmitted beam 38a and 38b, respectively, is transmitted from volumetric segment 34a and 34b, respectively, and then transmitted through second side 36a and 36b, respectively, of transparent passageway 22, and then detected and received by transmitted beam first and second detectors 90a and 90b, and, 92a and 92b, respectively, for forming detected rod material volumetric segment transmitted beam 38'a and 38'b, respectively.

Detection unit temperature sensor, $TS_d$, 100a and 100b, respectively, generates a detection unit temperature sensor output signal proportional to the sensed temperature in the critical region of operation of detection unit 40a and 40b, respectively, and sends the detection unit temperature sensor output signal to detection unit temperature sensor signal amplifier 102a and 102b, respectively. In general, detection unit temperature sensor, $TS_d$, 100a and 100b, respectively, is any appropriately compact or miniature sized and configured temperature sensing device, mechanism, or component, for example, a thermocouple, capable of sensing temperature, and generating an electrical or electronic signal corresponding and proportional to the sensed temperature. For process design, process control, and reference purposes, calibration data and information correlating a range of values of the input sensed temperature with a corresponding range of values of the corresponding detection unit temperature sensor output signal, are empirically determined using standardized conditions of operating electro-optical transmission module 24a and 24b, respectively.

Detection unit temperature sensor signal amplifier 102a and 102b, respectively, receives the detection unit temperature sensor output signal sent from detection unit temperature sensor, $TS_d$, 100a and 100b, respectively, and amplifies the detection unit temperature sensor output signal. The amplified detection unit temperature sensor output signal is sent to detection unit signal comparator 104a and 104b, respectively.

Detection unit signal comparator 104a and 104b, respectively, receives the amplified detection unit temperature sensor output signal sent from detection unit temperature sensor signal amplifier 102a and 102b, respectively, and receives the detection unit signal integrator output signal sent from detection unit signal integrator 98a and 98b, respectively. Detection unit signal comparator 104a and 104b, respectively, then compares, and adds or subtracts, in a temperature compensative manner, the value of the amplified detection unit temperature sensor output signal, to or from, respectively, the value of the detection unit signal integrator output signal, according to the magnitude and the direction or sign (positive or negative) of the temperature change represented by the amplified detection unit temperature sensor output signal, for generating a detection unit signal comparator output signal, herein, also referred to as a detection unit temperature change compensated output signal, which is sent to detection unit output signal buffer 106a and 106b, respectively.

Detection unit output signal buffer 106a and 106b, respectively, in the second specific configuration of detection unit 40a and 40b, respectively, in electro-optical transmission module 24a and 24b, respectively, of electro-optical inspection device 60, receives the detection unit signal comparator output signal (detection unit temperature change compensated output signal) sent from detection unit signal comparator 104a and 104b, respectively, and stores the detection unit signal comparator output signal (detection unit temperature change compensated output signal) in the form of a stored detection unit temperature change compensated output signal 106'a and 106'b, respectively. Stored detection unit temperature change compensated output signals 106'a and 106'b are sent to a process control and data analysis unit, for example, process control and data analysis unit 120, as shown in FIG. 2, for determining the internal properties and characteristics, such as density, structure, defects, and impurities, and variabilities thereof, of longitudinally moving rod of material 12. The determined internal properties and characteristics of moving rod of material 12 are useable by a process control and data analysis unit, for example, process control and data analysis unit 120, for controlling the process of electro-optically inspecting moving rod of material 12, and/or for controlling downstream processing of longitudinally moving rod of material 12.

Detection unit component connections and linkages 108a and 108b, respectively, in the second specific configuration of detection unit 40a and 40b, respectively, in electro-optical transmission module 24a and 24b, respectively, of electro-optical inspection device 60, operatively connect and link the components, in particular, (1) transmitted beam first detector 90a and 90b, respectively, (2) transmitted beam second detector 92a and 92b, respectively, (3) transmitted beam signal first amplifier 94a and 94b, respectively, (4) transmitted beam signal second amplifier 96a and 96b, respectively, (5) detection unit signal integrator 98a and 98b, respectively, (6) detection unit signal buffer 106a and 106b, respectively, and additional components, (8) detection unit temperature sensor, $TS_d$, 100a and 100b, respectively, (9) detection unit temperature sensor signal amplifier 102a and 102b, respectively, and (10) detection unit signal comparator 104a and 104b, respectively, included in the second specific configuration of detection unit 40a and 40b, respectively, in the form of an electro-optical detection circuit which includes monitoring and compensating for temperature changes.

In the second specific configuration of detection unit 40a and 40b, respectively, in electro-optical transmission module 24a and 24b, respectively, of electro-optical inspection device 60, the additional components, (8) detection unit temperature sensor, $TS_d$, 100a and 100b, respectively, (9) detection unit temperature sensor signal amplifier 102a and 102b, respectively, and (10) detection unit signal comparator 104a and 104b, respectively, form a temperature change monitoring and compensating electro-optical detection sub-circuit, based upon, and in accordance with, operation of the strategically located detection unit temperature sensor, $TS_d$, 100a and 100b, respectively, and operatively coupled detection unit signal comparator 104a and 104b, respectively, and associated electro-optical circuitry, included in detection unit 40a and 40b, respectively, involving the detection unit temperature sensor output signal sent by detection unit temperature sensor, $TS_d$, 100a and 100b, respectively, which in turn, is proportional to the sensed temperature in the critical region of operation of detection unit 40*a* and 40*b*, respectively. Thus, overall operation of each detection unit 40*a* and 40*b*, respectively, is based on, and in accordance with, a temperature change monitoring and compensating electro-optical detection circuit.

Automatic operations of each detection unit 40*a* and 40*b*, in general, and of the above described electrical and electronic components and elements thereof, in each electro-optical transmission module 24*a* and 24*b*, respectively of electro-optical inspection device 60, are performed by a process control and data analysis unit, such as process control and data analysis unit 120.

In FIG. 2, with reference to reference XYZ coordinate system 50, it is shown that the first of the two electro-optical transmission modules, that is, electro-optical transmission module 24*a*, in general, including illumination unit 26*a*, detection unit 40*a*, and preferably, a housing 42*a* of selected components of these units, of electro-optical inspection device 60, are geometrically configured, positioned, and operative, such that electromagnetic radiation source beam 44*a* generated by illumination unit 26*a* is focused, via focusing lens 46*a*, in the negative Y-direction towards first side 30*a* (perspectively viewed and understood as from above and towards the top side) of transparent passageway 22 and is also incident, via polarizing beam splitter 48*a*, in the negative Y-direction upon rod of material 12 longitudinally moving in the positive Z-direction along coaxial optical path 20 within transparent passageway 22. Accordingly, incident focused beam 32*a* illuminates, in the negative Y-direction, volumetric segment 34*a* of longitudinally moving rod of material 12, such that at least part of incident focused beam 32*a* is affected by and transmitted in the negative Y-direction through volumetric segment 34*a*, and then transmitted in the negative Y-direction through second side 36*a* (perspectively viewed and understood as through the bottom side) of transparent passageway 22, for forming rod material volumetric segment transmitted beam 38*a*. Rod material volumetric segment transmitted beam 38*a* is detected by detection unit 40*a*, for forming detected rod material volumetric segment transmitted beam 38'*a* useable for determining the internal properties and characteristics of the longitudinally moving rod of material 12.

Additionally in FIG. 2, with reference to reference XYZ coordinate system 50, it is shown that the second of the two electro-optical transmission modules, that is, electro-optical transmission module 24*b*, in general, including illumination unit 26*b*, detection unit 40*b*, and preferably, a housing 42*b* of selected components of these units, of electro-optical inspection device 60, are geometrically configured, positioned, and operative, such that electromagnetic radiation source beam 44*b* generated by illumination unit 26*b* is focused, via focusing lens 46*b*, in the positive X-direction towards first side 30*b* (perspectively viewed and understood as from behind and towards the back side) of transparent passageway 22 and is also incident, via polarizing beam splitter 48*b*, in the positive X-direction upon rod of material 12 longitudinally moving in the positive Z-direction along coaxial optical path 20 within transparent passageway 22. Accordingly, incident focused beam 32*b* illuminates, in the positive X-direction, volumetric segment 34*b* of longitudinally moving rod of material 12, such that at least part of incident focused beam 32*b* is affected by and transmitted in the positive X-direction through volumetric segment 34*a*, and then transmitted in the positive X-direction through second side 36*a* (perspectively viewed and understood as through the front side) of transparent passageway 22, for forming rod material volumetric segment transmitted beam 38*b*. Rod material volumetric segment transmitted beam 38*b* is detected by detection unit 40*b*, for forming detected rod material volumetric segment transmitted beam 38'*b* useable for determining the internal properties and characteristics of the longitudinally moving rod of material 12.

As clearly shown in FIG. 2, with reference to reference XYZ coordinate system 50, in electro-optical inspection device 60, the longitudinal and angular, radial, or circumferential, positions or locations of the first and second electro-optical transmission modules 24*a* and 24*b*, in general, and, of illumination units 26*a* and 26*b*, detection units 40*a* and 40*b*, and housings 42*a* and 42*b* of selected components of these units, respectively, in particular, relative to each other, and relative to the same transparent passageway 22 within which extends the same coaxial optical path 20, are spatially staggered or displaced along the coaxial optical path 20, along which the longitudinally moving rod of material 12 is guided by the rod guiding unit 14.

More specifically, in electro-optical inspection device 60, each of the two electro-optical transmission modules 24*a* and 24*b*, including respective units and components thereof, through which passes the same coaxial optical path 20 and the same coaxial transparent passageway 22, is positioned at a different longitudinal (spatial) position or location in the Z-direction around and along transparent passageway 22 within which extends coaxial optical path 20. Additionally, at each different longitudinal (spatial) position or location in the Z-direction around and along transparent passageway 22, each of the two electro-optical transmission modules 24*a* and 24*b*, including respective units and components thereof, is positioned at a different angular, radial, or circumferential, position or location in the XY-plane around transparent passageway 22. In the particular embodiment of electro-optical inspection device 60, illustrated in FIG. 2, at the different longitudinal (spatial) positions or locations in the Z-direction around and along transparent passageway 22, the angular, radial, or circumferential, positions or locations of the two electro-optical transmission modules 24*a* and 24*b*, including respective units and components thereof, relative to each other, in the XY-plane around transparent passageway 22, differ by a right angle or 90 degrees.

In electro-optical inspection device 60, spatially staggering or displacing the positions or locations of electro-optical transmission modules 24*a* and 24*b* significantly decreases potential cross interferences among the various electromagnetic radiation beams emanating from, propagating through, transmitted into, out of, or through, and, entering into or exiting out of, illumination units 26*a* and 26*b*, respectively, first side 30*a* and 30*b*, respectively, and second side 36*a* and 36*b*, respectively, of transparent passageway 22, volumetric segments 34*a* and 34*b*, respectively, of moving rod of material 12, and detection units 40*a* and 40*b*, respectively, of electro-optical transmission modules 24*a* and 24*b*, respectively.

Additionally, the procedure of spatially staggering or displacing enables each volumetric segment 34*a* and 34*b* of longitudinally moving rod of material 12 to be inspected for a sufficiently integratable amount of time by illumination unit 26*a*/detection unit 40*a* pair, and by illumination unit 26*b*/detection unit 40*b* pair, respectively, of each electro-optical transmission module 24*a* and 24*b*, respectively. These factors contribute to achieving higher speed, sensitivity, signal to noise ratios, accuracy, and precision, and therefore, overall performance, of the electro-optical inspection method implemented by using electro-optical inspection device 60, having two electro-optical transmission modules 24*a* and 24*b*, in the second exemplary specific preferred embodiment illustrated in FIG. 2, compared to using electro-optical inspection device 10, having a single electro-optical transmission module 24, in the first exemplary specific preferred embodiment illustrated in FIG. 1, of the generalized electro-optical inspection device for electro-optically inspecting and determining internal properties and characteristics of the longitudinally moving rod of material 12.

Herein following are illustratively described further details, and, additional, alternative, and optional, features, of the steps and sub-steps of the generalized electro-optical inspection method, and of the components, elements, operation, and implementation, of the generalized electro-optical inspection device, of the present invention, with reference to the first and second exemplary specific preferred embodiments of the generalized electro-optical inspection device, electro-optical inspection devices 10 and 60, of the present invention, as illustrated in FIGS. 1 and 2, respectively.

In electro-optical inspection devices 10 and 60, of the first and second exemplary specific preferred embodiments, respectively, of the generalized device for electro-optically inspecting and determining internal properties and characteristics of a longitudinally moving rod of material, that is, longitudinally moving rod of material 12, as illustrated in FIGS. 1 and 2, respectively, each electro-optical transmission module (24 in FIG. 1; 24a and 24b, respectively, in FIG. 2) preferably, further includes: (iii) a module housing (42 in FIG. 1; 42a and 42b, respectively, in FIG. 2).

Module housing (42 in FIG. 1; 42a and 42b, respectively, in FIG. 2), through which passes transparent housing 62 of rod guiding unit 14, is for operatively supporting or holding transparent housing 62 which houses, holds, or confines, transparent passageway 22 within which is coaxial optical path 20, along which is guided longitudinally moving rod of material 12. In addition to enabling through passage of transparent housing 62, module housing (42 in FIG. 1; 42a and 42b, respectively, in FIG. 2) is for operatively housing or holding selected components of illumination unit (26 in FIG. 1; 26a and 26b, respectively, in FIG. 2) and of detection unit (40 in FIG. 1; 40a and 40b, respectively, in FIG. 2). In particular, the additional main components, polarizing beam splitter (48 in FIG. 1; 48a and 48b, respectively, in FIG. 2), optical feedback reference beam detector (74 in FIG. 1; 74a and 74b, respectively, in FIG. 2), and illumination unit temperature sensor, $TS_i$, (78 in FIG. 1; 78a and 78b, respectively, in FIG. 2), in the second specific configuration of illumination unit (26 in FIG. 1; 26a and 26b, respectively, in FIG. 2), and in particular, the main components, transmitted beam first detector (90 in FIG. 1; 90a and 90b, respectively, in FIG. 2) and transmitted beam second detector (92 in FIG. 1; 92a and 92b, respectively, in FIG. 2), in each of the first and second specific configurations of detection unit (40 in FIG. 1; 40a and 40b, respectively, in FIG. 2), and the additional main component, detection unit temperature sensor, $TS_d$, (100 in FIG. 1; 100a and 100b, respectively, in FIG. 2), in the second specific configuration of detection unit (40 in FIG. 1; 40a and 40b, respectively, in FIG. 2).

Module housing (42 in FIG. 1; 42a and 42b, respectively, in FIG. 2) is, preferably, of a square or rectangular geometrical shape, having a preferably tubular or cylindrical opening or hole (to be clearly understood as being present, but not explicitly shown in FIGS. 1 and 2), geometrically appropriate for through passage of tubular or cylindrical shaped transparent housing 62. Module housing (42 in FIG. 1; 42a and 42b, respectively, in FIG. 2) is constructed from a metallic material, for example, aluminum, a non-metallic material, a composite material, or a combination thereof, and is configured for enabling operative supporting or holding of transparent housing 62, as well as for enabling operative housing or holding of selected components of illumination unit (26 in FIG. 1; 26a and 26b, respectively, in FIG. 2) and of detection unit (40 in FIG. 1; 40a and 40b, respectively, in FIG. 2).

While electro-optically inspecting longitudinally moving rod of material 12, temperature changes typically occur in critical regions of module housing (42 in FIG. 1; 42a and 42b, respectively, in FIG. 2) in each electro-optical transmission module (24 in FIG. 1; 24a and 24b, respectively, in FIG. 2) of electro-optical inspection devices 10 and 60, respectively, particularly in the immediate vicinity of the electro-optically inspected volumetric segment (34 in FIG. 1; 34a and 34b, respectively, in FIG. 2) of moving rod of material 12. Magnitudes of such temperature changes may be sufficiently large so as to significantly increase noise and error levels during the electro-optical inspection process, which may translate to meaningful decreases in accuracy and precision of the results obtained from the electro-optical inspection process.

For achieving higher sensitivity, signal to noise ratios, accuracy, and precision, and therefore, overall performance, of the first specific configuration of each illumination unit (26 in FIG. 1; 26a and 26b, respectively, in FIG. 2), and of each of the first and second specific configurations of each detection unit (40 in FIG. 1; 40a and 40b, respectively, in FIG. 2), in each electro-optical transmission module (24 in FIG. 1; 24a and 24b, respectively, in FIG. 2) of electro-optical inspection devices 10 and 60, respectively, preferably, each module housing (42 in FIG. 1; 42a and 42b, respectively, in FIG. 2) further includes components, in particular, at least one strategically located module housing temperature sensor, $TS_h$, (110 in FIG. 1; 110a and 110b, respectively, in FIG. 2) and associated electro-optical circuitry, and, sub-steps and procedures, implemented via corresponding algorithms and software programs, for operating thereof, for monitoring temperature, typically, in the range of between about 50° C. and 60° C., and compensating for temperature changes in critical regions of module housing (42 in FIG. 1; 42a and 42b, respectively, in FIG. 2) in each electro-optical transmission module (24 in FIG. 1; 24a and 24b, respectively, in FIG. 2) of electro-optical inspection devices 10 and 60, respectively. Such critical regions of operation are particularly in the immediate vicinity of the electro-optically inspected volumetric segment (34 in FIG. 1; 34a and 34b, respectively, in FIG. 2) of rod of material 12, longitudinally moving along optical path 20 within transparent passageway 22 housed by transparent housing 62, during the electro-optical inspection process.

Module housing temperature sensor, $TS_h$, (110 in FIG. 1; 110a and 110b, respectively, in FIG. 2) generates a module housing temperature sensor output signal proportional to the sensed temperature in the critical region of module housing (42 in FIG. 1; 42a and 42b, respectively, in FIG. 2), and sends the module housing temperature sensor output signal to a module housing temperature sensor output signal buffer (112 in FIG. 1; 112a and 112b, respectively, in FIG. 2). In general, module housing temperature sensor, $TS_h$, (110 in FIG. 1; 110a and 110b, respectively, in FIG. 2) is any appropriately compact or miniature sized and configured temperature sensing device, mechanism, or component, for example, a thermocouple, capable of sensing temperature, and generating an electrical or electronic signal corresponding and proportional to the sensed temperature. For process design, process control, and reference purposes, calibration data and information correlating a range of values of the input sensed temperature with a corresponding range of values of the corresponding module housing temperature sensor output signal, are empirically determined using standardized conditions of operating each electro-optical transmission module (24 in FIG. 1; 24a and 24b, respectively, in FIG. 2).

Module housing temperature sensor output signal buffer (112 in FIG. 1; 112a and 112b, respectively, in FIG. 2), in each electro-optical transmission module (24 in FIG. 1; 24a and 24b, respectively, in FIG. 2) of electro-optical inspection devices 10 and 60, respectively, receives the module housing temperature sensor output signal sent from module housing temperature sensor, $TS_h$, (110 in FIG. 1; 110a and 110b, respectively, in FIG. 2), and stores the module housing temperature sensor output signal in the form of a stored module housing temperature sensor output signal (112' in FIG. 1; 112'a and 112'b, respectively, in FIG. 2). Stored module housing temperature sensor output signal (112' in FIG. 1; 112'a and 112'b, respectively, in FIG. 2) is sent to a process control and data analysis unit, for example, process control and data analysis unit 120, as shown in FIGS. 1 and 2.

Stored module housing temperature sensor output signal (112' in FIG. 1; 112'a and 112'b, respectively, in FIG. 2) is used for correcting, in a temperature compensative manner, the stored detection unit output signal (106' in FIG. 1; 106'a and 106'b, respectively, in FIG. 2) which is also sent to process control and data analysis unit 120, as previously described above, from detection unit output signal buffer (106 in FIG. 1; 106a and 106b, respectively, in FIG. 2) of detection unit (40 in FIG. 1; 40a and 40b, respectively, in FIG. 2) in each electro-optical transmission module (24 in FIG. 1; 24a and 24b, respectively, in FIG. 2) of electro-optical inspection devices 10 and 60, respectively.

More specifically, process control and data analysis unit 120 compares, and adds or subtracts, in a temperature compensative manner, the value of the stored module housing temperature sensor output signal (112' in FIG. 1; 112'a and 112'b, respectively, in FIG. 2), to or from, respectively, the value of the stored detection unit output signal (106' in FIG. 1; 106'a and 106'b, respectively, in FIG. 2), according to the magnitude and the direction or sign (positive or negative) of the temperature change represented by the stored module housing temperature sensor output signal (112' in FIG. 1; 112'a and 112'b, respectively, in FIG. 2), for generating a 'corrected' detection unit output signal, which is stored and used by process control and data analysis unit 120 for determining the internal properties and characteristics, such as density, structure, defects, and impurities, and variabilities thereof, of longitudinally moving rod of material 12. The determined internal properties and characteristics of moving rod of material 12 are then useable by a process control and data analysis unit, for example, process control and data analysis unit 120, for controlling the process of electro-optically inspecting moving rod of material 12, and/or for controlling downstream processing of longitudinally moving rod of material 12.

As previously stated above, the present invention is directed to commercial applications requiring real time, non-invasive, high speed, high sensitivity, low noise, high accuracy, high precision, temperature compensative, and low vibration, measuring and analyzing of internal properties and characteristics of a continuously or intermittently longitudinally moving rod of material, as the rod of material is transported or conveyed during a commercial manufacturing sequence, particularly a manufacturing sequence including quality control and/or quality assurance processes.

Monitoring temperature and compensating for temperature changes in critical regions of operation of the illumination unit (26 in FIG. 1; 26a and 26b, respectively, in FIG. 2), of the detection unit (40 in FIG. 1; 40a and 40b, respectively, in FIG. 2), and preferably, also of module housing (42 in FIG. 1; 42a and 42b, respectively, in FIG. 2), in the electro-optical transmission module (24 in FIG. 1; 24a and 24b, respectively, in FIG. 2) in electro-optical inspection devices 10 and 60, of the first and second exemplary specific preferred embodiments, respectively, of the generalized device for electro-optically inspecting and determining internal properties and characteristics of a longitudinally moving rod of material, that is, longitudinally moving rod of material 12, as illustrated in FIGS. 1 and 2, respectively, of the present invention, are previously described above.

In general, while electro-optically inspecting a longitudinally moving rod of material, the longitudinally moving rod of material, in general, and the electro-optically inspected section or segment of the longitudinally moving rod of material, in particular, typically vibrates, particularly, in the radial direction. For example, with respect to implementation of the electro-optical inspection method and device of the present invention, as illustratively described above, with reference to FIGS. 1 and 2, while electro-optically inspecting longitudinally moving rod of material 12, longitudinally moving rod of material 12, in general, and the electro-optically inspected volumetric segment (34 in FIG. 1; 34a and 34b, respectively, in FIG. 2), in particular, typically vibrates, particularly, in the radial direction. With reference to reference XYZ coordinate system 50, such radial vibrating occurs in the XY-plane of moving rod of material 12. Magnitudes of such radially directed vibrating may be sufficiently large so as to significantly increase noise and error levels during the illumination and detection processes, which may translate to meaningful decreases in accuracy and precision of the results obtained from the electro-optical inspection process.

With respect to the generalized electro-optical inspection method of the present invention, for achieving higher sensitivity, signal to noise ratios, accuracy, and precision, and therefore, overall performance, of steps (a) through (d) in the generalized electro-optical inspection method, preferably, a specific preferred embodiment of the generalized electro-optical inspection method further includes sub-steps and procedures, and components for performing thereof, for preventing, eliminating, or at least reducing, radially directed vibrating of longitudinally moving rod of material 12, in general, and of the electro-optically inspected volumetric segment (34 in FIG. 1; 34a and 34b, respectively, in FIG. 2) of longitudinally moving rod of material 12, in particular, during the electro-optical inspection process.

In particular, preferably, following step (a) and preceding step (b) in the generalized electro-optical inspection method of the present invention, as described above, there is inserted the step of generating a continuous vortical type of flow of gas within and along transparent passageway 22 by a vortex generating mechanism, preferably, included as a component of rod guiding unit 14, such that the flowing gas rotates as a vortex around optical path 20 and around moving rod of material 12, and flows downstream within and along transparent passageway 22 in the same longitudinal direction of moving rod of material 12, such that the flowing gas radially impinges upon longitudinally moving rod of material 12 within transparent passageway 22. The flowing gas radially impinging upon longitudinally moving rod of material 12 prevents, eliminates, or reduces, radially directed vibrating of longitudinally moving rod of material 12 during operation of rod guiding unit 14 and during operation of electro-optical transmission module (24 in FIG. 1; 24a and 24b, respectively, in FIG. 2), during the electro-optically inspecting and determining of the internal properties and characteristics of longitudinally moving rod of material 12.

With respect to the generalized electro-optical inspection device of the present invention, for achieving higher sensitivity, signal to noise ratios, accuracy, and precision, and therefore, overall performance, of operation of rod guiding unit 14 and of each electro-optical transmission module (24 in FIG. 1; 24a and 24b, respectively, in FIG. 2) in electro-optical inspection devices 10 and 60, of the first and second exemplary specific preferred embodiments, respectively, of the generalized device for electro-optically inspecting and determining internal properties and characteristics of a longitudinally moving rod of material, that is, longitudinally moving rod of material 12, as illustrated in FIGS. 1 and 2, respectively, preferably, rod guiding unit 14 further includes components, and, sub-steps and procedures for operating thereof, for preventing, eliminating, or at least reducing, radially directed vibrating of longitudinally moving rod of material 12, in general, and of the electro-optically inspected volumetric segment 34 of longitudinally moving rod of material 12, in particular, during the electro-optical inspection process.

Accordingly, in a specific, more preferred, configuration of rod guiding unit 14 in electro-optical inspection devices 10 and 60, of the first and second exemplary specific preferred embodiments, respectively, for electro-optically inspecting and determining internal properties and characteristics of longitudinally moving rod of material 12, as illustrated in FIGS. 1 and 2, respectively, rod guiding unit 14 includes the main components: (i) transparent housing 62, (ii) rod material entrance assembly 64, and further includes additional main component: (iii) a vortex generating mechanism 130.

In this specific, more preferred, configuration of rod guiding unit 14 in electro-optical inspection devices 10 and 60, structure and function of transparent housing 62, and of rod material entrance assembly 64, operatively attached or connected to transparent housing 62, are the same as previously described above.

Vortex generating mechanism 130 is for generating a continuous vortical type of flow of gas (indicated in FIGS. 1 and 2 by the alternating circularly curved pairs and parallel pairs of solid head reference arrows 132), within and along transparent passageway 22, in particular, extending between rod material entrance area 16 and rod material exit area 18, of rod guiding unit 14 in each electro-optical inspection device 10 and 60, such that flowing gas 132 rotates as a vortex around optical path 20 and around moving rod of material 12, and flows downstream within and along transparent passageway 22 in the same longitudinal direction of moving rod of material 12 (for example, as shown in FIGS. 1 and 2, in the Z-direction), such that the flowing gas radially impinges upon longitudinally moving rod of material 12 within transparent passageway 22.

Flowing gas 132 radially impinging upon longitudinally moving rod of material 12 prevents, eliminates, or reduces, radially directed vibrating of longitudinally moving rod of material 12, in general, and of the electro-optically inspected volumetric segment (34 in FIG. 1; 34a and 34b, respectively, in FIG. 2) of longitudinally moving rod of material 12, in particular, during operation of rod guiding unit 14 and during operation of each electro-optical transmission module (24 in FIG. 1; 24a and 24b, respectively, in FIG. 2), during the electro-optically inspecting and determining of the internal properties and characteristics of longitudinally moving rod of material 12.

As shown in FIGS. 1 and 2, in rod guiding unit 14, preferably, vortex generating mechanism 130 is operatively connected to rod material entrance assembly 64, such that the gas, for example, air, used for generating the continuous vortical type of flow of gas 132 enters rod guiding unit 14, via rod material entrance assembly 64, in the same general region that moving rod of material 12 enters rod guiding unit 14 of each electro-optical inspection device 10 and 60. For example, as shown in FIGS. 1 and 2, vortex generating mechanism 130 is operatively connected to a side of rod material entrance assembly 64, such that the gas used for generating the continuous vortical type of flow of gas 132 enters rod guiding unit 14, via the side of rod material entrance assembly 64, in the same general region that moving rod of material 12 enters rod guiding unit 14 of each electro-optical inspection device 10 and 60. More specifically, for example, as also shown in FIGS. 1 and 2, vortex generating mechanism 130 is operatively connected to a side of rod material entrance assembly 64, such that the gas used for generating the continuous vortical type of flow of gas 132 enters rod guiding unit 14, via the side of rod material entrance assembly 64, in the same general region that moving rod of material 12 enters rod guiding unit 14, and in a direction (for example, in the radial, Y-direction or X-direction) which is orthogonal to the longitudinal direction (for example, the Z-direction) of movement of moving rod of material 12 which is longitudinally moved by rod moving unit 5 and longitudinally guided by rod guiding unit 14.

In rod guiding unit 14, vortex generating mechanism 130 includes the main components: (1) a gas supply 134, (2) a gas intake/output pump 136, and (3) a gas flow directing channel 138.

The gas in gas supply 134 used for generating the continuous vortical type of flow of gas 132 is, for example, air, or another gas, for example, an inert gas such as nitrogen, helium, or argon. The gas is non-chemically reactive, or at most, minimally or insignificantly chemically reactive, with the material making up moving rod of material 12, as well as with the material of construction of transparent housing 62, in order to prevent contamination of either of these during the electro-optical inspection process.

Gas intake/output pump 136 is for taking or pumping in the gas supplied by gas supply 134, and for outputting or pumping out the taken or pumped in gas, in the form of a flowing gas. Preferably, the pressure, and the linear flow velocity, of the gas output or pumped out of gas intake/output pump 136 and, flowing into rod material entrance assembly 64 and into transparent housing 62, is on the order of about one atmosphere above room atmospheric pressure, and on the order of about 100 meters per minute, respectively. Such pressure and linear flow velocity of the flowing gas are also maintained within and along transparent passageway 22.

Gas flow directing channel 138, operatively connected to gas intake/output pump 136 and to rod material entrance assembly 64, is for directing and channeling the gas taken or pumped in by gas intake/output pump 136, and for directing and channeling the flowing gas output or pumped out by gas intake/output pump 136 into rod material entrance assembly 64 and into transparent housing 62, such that a continuous vortical type of flow of gas 132 is generated within and along transparent passageway 22, in particular, extending between rod material entrance area 16 and rod material exit area 18, of rod guiding unit 14. Gas flow directing channel 138 is of a variable geometrical configuration or form, and is constructed from a metallic material, a non-metallic material, a composite material, or a combination thereof, for enabling operative attachment or connection to transparent housing 62, and for enabling directing and channeling of the flowing gas output or pumped out by gas intake/output pump 136 into rod material entrance assembly 64 and into transparent housing 62.

Accordingly, during operation of vortex generating mechanism 130, as part of operation of rod guiding unit 14, gas intake/output pump 136 takes or pumps in the gas supplied by gas supply 134, as indicated in FIGS. 1 and 2 by 140, and outputs or pumps out the taken or pumped in gas, in the form of a flowing gas. The flowing gas is then directed and channeled via gas flow directing channel 138 into rod material entrance assembly 64 and into transparent housing 62, such that a continuous vortical type of flow of gas 132 is generated within and along transparent passageway 22, in particular, extending between rod material entrance area 16 and rod material exit area 18, of rod guiding unit 14. The continuous vortical type of flowing gas 132 radially impinging upon longitudinally moving rod of material 12 prevents, eliminates, or reduces, radially directed vibrating of longitudinally moving rod of material 12, in general, and of the electro-optically inspected volumetric segment (34 in FIG. 1; 34a and 34b, respectively, in FIG. 2) of longitudinally moving rod of material 12, in particular, during operation of rod guiding unit 14 and during operation of each electro-optical transmission module (24 in FIG. 1; 24a and 24b, respectively, in FIG. 2), during the electro-optically inspecting and determining of the internal properties and characteristics of longitudinally moving rod of material 12. The continuous vortical type of flow of gas 132 continuously exits transparent passageway 22, in particular, at rod material exit area 18, of rod guiding unit 14, as indicated by 142.

Accordingly, operation of vortex generating mechanism 130, as part of operation of rod guiding unit 14, corresponds to a kind of 'gas bearing' which assists in producing a smooth and stable longitudinal movement of moving rod of material 12 along optical path 20 within transparent passageway 22, during the entire electro-optical inspection process.

A secondary function of vortex generating mechanism 130, as part of operation of rod guiding unit 14, is that of cleaning rod guiding unit 14, in general, and that of cleaning transparent passageway 22 within transparent housing 62, in particular, during the electro-optical inspection process. The cleaning function of vortex generating mechanism 130 is a consequence of the continuous vortical type of flow of gas 132 flowing within and along transparent passageway 22, within transparent housing 62, in particular, from rod material entrance area 16 to rod material exit area 18, of rod guiding unit 14.

The above illustratively described vortex generating mechanism 130, as part of operation of a rod guiding unit, for example, rod guiding unit 14 of the present invention, is generally applicable for preventing, eliminating, or reducing, radially directed vibrating of a longitudinally moving rod of material during electro-optically inspecting the longitudinally moving rod of material, and is not specifically limited to use only with the generalized electro-optical inspection method and the corresponding generalized electro-optical inspection device of the present invention. More specifically, the above illustratively described vortex generating mechanism 130, is applicable for use with prior art electro-optical inspection methods, devices, and apparatuses.

Accordingly, the present invention also features a method for preventing, eliminating, or reducing, radially directed vibrating of a longitudinally moving rod of material during electro-optically inspecting the longitudinally moving rod of material, including the steps of: (a) guiding the longitudinally moving rod of material along its longitudinal axis by a rod guiding unit, along an optical path within a transparent passageway, where the optical path and the transparent passageway coaxially extend along the longitudinal axis of the longitudinally moving rod of material and pass through an electro-optical inspection apparatus used for electro-optically inspecting the longitudinally moving rod of material; and (b) generating a continuous vortical type of flow of gas within and along the transparent passageway by a vortex generating mechanism, such that the flowing gas rotates as a vortex around the optical path and around the longitudinally moving rod of material, and flows downstream within and along the transparent passageway in the same longitudinal direction of the longitudinally moving rod of material, such that the flowing gas radially impinges upon the longitudinally moving rod of material within the transparent passageway. The flowing gas radially impinging upon the longitudinally moving rod of material prevents, eliminates, or reduces, radially directed vibrating of the longitudinally moving rod of material during the electro-optically inspecting the longitudinally moving rod of material.

Accordingly, the present invention also features a device for preventing, eliminating, or reducing, radially directed vibrating of a longitudinally moving rod of material during electro-optically inspecting the longitudinally moving rod of material, the device being a rod guiding unit for guiding the longitudinally moving rod of material along its longitudinal axis, along an optical path within a transparent passageway, where the optical path and the transparent passageway coaxially extend along the longitudinal axis of the longitudinally moving rod of material and pass through an electro-optical inspection apparatus used for electro-optically inspecting the longitudinally moving rod of material, where the rod guiding unit includes a vortex generating mechanism for generating a continuous vortical type of flow of gas within and along the transparent passageway, such that the flowing gas rotates as a vortex around the optical path and around the longitudinally moving rod of material, and flows downstream within and along the transparent passageway in the same longitudinal direction of the longitudinally moving rod of material, such that the flowing gas radially impinges upon the longitudinally moving rod of material within the transparent passageway. The flowing gas impinging upon the longitudinally moving rod of material prevents, eliminates, or reduces, radially directed vibrating of the longitudinally moving rod of material, during the electro-optically inspecting the longitudinally moving rod of material.

For automatically controlling the process, and analyzing the data, of the generalized electro-optical inspection method and corresponding device, of the present invention, the present invention further includes process control and data analysis steps, sub-steps, and procedures, implemented via corresponding process control and data analysis algorithms and software programs, and components for performing thereof, in particular, a process control and data analysis unit, such as process control and data analysis unit 120, as shown in FIGS. 1 and 2.

Process control and data analysis unit 120 supplies necessary or appropriate levels of power to each electrically or electronically activated unit, component, mechanism, and element, of electro-optical inspection devices 10 and 60 (indicated only in FIG. 1, but equally applicable in FIG. 2, by the small dotted line and unfilled in circle 'background' power grid 150, connecting each electrically or electronically operable unit, component, mechanism, and element, of electro-optical inspection devices 10 and, 60 to process control and data analysis unit 120).

Rod moving unit 5 either includes, or is operatively connected to, a rod moving unit mechanism 7, which, in addition to being involved in the electro-mechanics of moving rod of material 12, provides a real time rod moving unit clock signal 9 to process control and data analysis unit 120, that includes data and information about the rate or linear speed at which rod moving unit 5 moves rod of material 12. Such data and information is needed for synchronizing both process control and data analysis of the electro-optical inspection process. In particular, inspection time of the electro-optically inspected volumetric segment (34 in FIG. 1; 34a and 34b, respectively, in FIG. 2) of longitudinally moving rod of material 12, is a function of both the rate or linear speed at which rod moving unit 5 moves rod of material 12, and of the actual length of the moving rod of material 12.

Process control and data analysis unit 120 either includes, or is operatively connected to, a personal computer (PC) workstation 160, useable by an operator or controller of electro-optical inspection devices 10 and 16. A process control sub-unit 162 is operatively connected to process control and data analysis unit 120, for functioning as an intermediate point between process control and data analysis of electro-optical inspection devices 10 and 16, and, process control and data analysis of further downstream processes, including for example, a rod cutting process and a rod segment rejecting process, involving operation of a rod cutting unit 164 and a rod segment reject unit 166, respectively, as shown in FIGS. 1 and 2.

Thus, the present invention, as illustratively described and exemplified hereinabove, is generally applicable for inspecting and determining internal properties and characteristics of a variety of different types of a rod of material, as long as the rod of material exhibits the behavior that an incident focused beam of electromagnetic radiation, while not altering the rod of material, is affected by and transmittable through volumetric segments of the rod of material. For example, but not limited to, a cigarette rod consisting of processed tobacco inside a rolled and sealed tube of cigarette wrapping paper. Moreover, the present invention is directed to commercial applications requiring real time, non-invasive, high speed, high sensitivity, low noise, high accuracy, high precision, temperature compensative, and low vibration, measuring and analyzing of internal properties and characteristics of a continuously or intermittently longitudinally moving rod of material, as the rod of material is transported or conveyed during a commercial manufacturing sequence, particularly a manufacturing sequence including quality control and/or quality assurance processes.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for electro-optically inspecting and determining internal properties and characteristics of a longitudinally moving rod of material, comprising the steps of:
   (a) guiding the longitudinally moving rod of material along its longitudinal axis by a rod guiding unit, along an optical path within a transparent passageway, said optical path and said transparent passageway coaxially extend along said longitudinal axis of the moving rod of material and pass through an electro-optical transmission module;
   (b) generating a focused beam of electromagnetic radiation by an illumination unit of said electro-optical transmission module, such that said focused beam is transmitted through a first side of said transparent passageway and incident upon the rod of material longitudinally moving within said transparent passageway;
   (c) illuminating a volumetric segment of the longitudinally moving rod of material by said incident focused beam, such that at least part of said incident focused beam is affected by and transmitted through said volumetric segment and then transmitted through a second side of said transparent passageway, for forming a rod material volumetric segment transmitted beam; and
   (d) detecting said rod material volumetric segment transmitted beam by a detection unit of said electro-optical transmission module, for forming a detected rod material volumetric segment transmitted beam; and
   (e) processing and analyzing said focused beam of step (b), said incident focused beam of step (c), and said rod material detected volumetric segment transmitted beam of step (d), by a process control and data analysis unit, for determining the internal properties and characteristics of the longitudinally moving rod of material.

2. The method of claim 1, wherein said incident focused beam is of electromagnetic radiation selected from the group consisting of infrared radiation, visible light, and ultraviolet radiation.

3. The method of claim 1, wherein said incident focused beam is of infrared electromagnetic radiation having wavelength in a range of between about 900 nm and about 1000 nm.

4. The method of claim 1, wherein said incident focused beam is of infrared electromagnetic radiation having wavelength in a range of between about 920 nm and about 970 nm.

5. The method of claim 1, wherein step (b), said generating said focused beam of electromagnetic radiation by said illumination unit includes a procedure for monitoring temperature and compensating for temperature changes in at least one critical region of operation of said illumination unit.

6. The method of claim 5, wherein a said critical region of operation is in immediate vicinity of said illuminated volumetric segment of the rod of material longitudinally moving along said optical path within said transparent passageway during the electro-optical inspection process.

7. The method of claim 5, wherein a said critical region of operation is in immediate vicinity where said incident focused beam is transmitted through said first side of said transparent passageway and incident upon said volumetric segment.

8. The method of claim 5, wherein step (b), said operation of said illumination unit including said procedure for monitoring temperature and compensating for temperature changes is based on a temperature change monitoring and compensating electro-optical feedback loop.

9. The method of claim 1, wherein step (d), said detecting said rod material volumetric segment transmitted beam by said detection unit further includes a procedure for monitoring temperature and compensating for temperature changes in at least one critical region of operation of said detection unit.

10. The method of claim 9, wherein a said critical region of operation is in immediate vicinity of said illuminated volumetric segment of the rod of material longitudinally moving along said optical path within said transparent passageway.

11. The method of claim 9, wherein a said critical region of operation is in immediate vicinity where said rod material volumetric segment transmitted beam is transmitted from said volumetric segment and then transmitted through said second side of said transparent passageway, and then detected and received by said detection unit.

12. The method of claim 9, wherein step (d), operation of said detection unit including said procedure for monitoring temperature and compensating for temperature changes is based on a temperature change monitoring and compensating electro-optical detection circuit.

13. The method of claim 1, wherein the internal properties and characteristics are density, structure, defects, and impurities, and variabilities thereof, of the longitudinally moving rod of material.

14. The method of claim 1, wherein said electro-optical transmission module includes a module housing through which passes said transparent passageway within which is said guided longitudinally moving rod of material.

15. The method of claim 14, further including a procedure for monitoring temperature and compensating for temperature changes in at least one critical region of operation of said module housing.

16. The method of claim 1, further including a procedure for preventing, eliminating, or reducing, radially directed vibrating of the longitudinally moving rod of material during electro-optically inspecting the longitudinally moving rod of material.

17. The method of claim 16, wherein said procedure includes generating a continuous vortical type of flow of gas within and along said transparent passageway by a vortex generating mechanism.

18. The method of claim 17, wherein pressure, and linear flow velocity, of said flow of gas are about one atmosphere above room atmospheric pressure, and about 100 meters per minute, respectively.

19. The method of claim 17, wherein operation of said vortex generating mechanism also cleans said rod guiding unit and cleans said transparent passageway during the electro-optical inspection process.

20. The method of claim 16, wherein said procedure includes generating a continuous vortical type of flow of gas within and along said transparent passageway by a vortex generating mechanism, such that said flowing gas rotates as a vortex around said optical path and around the longitudinally moving rod of material, and flows downstream within and along said transparent passageway in same longitudinal direction of the longitudinally moving rod of material, such that said flowing gas radially impinges upon the longitudinally moving rod of material within said transparent passageway, whereby said flowing gas radially impinging upon the longitudinally moving rod of material prevents, eliminates, or reduces, radially directed vibrating of the longitudinally moving rod of material during the electro-optically inspecting the longitudinally moving rod of material.

21. The method of claim 1, further including a procedure for cleaning said rod guiding unit and cleaning said transparent passageway during the electro-optical inspection process.

22. The method of claim 21, wherein said procedure includes generating a continuous vortical type of flow of gas within and along said transparent passageway by a vortex generating mechanism, whereby said flow of gas cleans said rod guiding unit and cleans said transparent passageway during the electro-optical inspection process.

23. The method of claim 1, wherein the longitudinally moving rod of material is a longitudinally moving cigarette rod.

24. The method of claim 1, wherein the longitudinally moving rod of material is a longitudinally moving cigarette rod consisting of processed tobacco inside a rolled and sealed tube of cigarette wrapping paper.

25. The method of claim 1, wherein step (a), said optical path and said transparent passageway coaxially extend along said longitudinal axis of the moving rod of material and pass through a plurality of more than one said electro-optical transmission module.

26. The method of claim 25, wherein each of said plurality of said electro-optical transmission modules is positionable at a different longitudinal position or location around and along said transparent passageway within which extends said optical path.

27. The method of claim 25, wherein each of said plurality of said electro-optical transmission modules is positionable at a same or different angular, radial, or circumferential, position or location around said transparent passageway within which extends said optical path.

28. The method of claim 25, wherein longitudinal and angular or circumferential positions of said plurality of said electro-optical transmission modules, relative to each other, and relative to said transparent passageway within which extends said optical path, are spatially staggered or displaced along said optical path, along which the longitudinally moving rod of material is guided by said rod guiding unit.

29. The method of claim 25, wherein each said electro-optical transmission module through which pass said optical path and said transparent passageway includes a paired said illumination unit and said detection unit.

30. The method of claim 29, wherein said paired illumination and detection units of said plurality of said electro-optical transmission modules are temporally continuously or discontinuously activated according to a pre-determined timing or switching schedule or sequence, while the longitudinally moving rod of material is continuously or intermittently moving and being guided through said plurality of electro-optical transmission modules.

31. The method of claim 30, wherein said pre-determined timing or switching schedule or sequence is effected via applying a synchronous or asynchronous on/off switching schedule or sequence for operating said paired illumination and detection units.

32. A method for preventing, eliminating, or reducing, radially directed vibrating of a longitudinally moving rod of material during electro-optically inspecting the longitudinally moving rod of material, comprising the steps of:
   (a) guiding the longitudinally moving rod of material along its longitudinal axis by a rod guiding unit, along an optical path within a transparent passageway, said optical path and said transparent passageway coaxially extend along said longitudinal axis of the longitudinally moving rod of material and pass through an electro-optical inspection apparatus used for electro-optically inspecting the longitudinally moving rod of material; and
   (b) generating a continuous vortical type of flow of gas within and along said transparent passageway by a vortex generating mechanism, such that said flowing gas rotates as a vortex around said optical path and around the longitudinally moving rod of material, and flows downstream within and along said transparent passageway in same longitudinal direction of the longitudinally moving rod of material, such that said flowing gas radially impinges upon the longitudinally moving rod of material within said transparent passageway;

whereby said flowing gas radially impinging upon the longitudinally moving rod of material prevents, eliminates, or reduces, radially directed vibrating of the longitudinally moving rod of material during the electro-optically inspecting the longitudinally moving rod of material.

33. The method of claim 32, wherein pressure, and linear flow velocity, of said flow of gas are about one atmosphere above room atmospheric pressure, and about 100 meters per minute, respectively.

34. A device for electro-optically inspecting and determining internal properties and characteristics of a longitudinally moving rod of material, comprising:
   (a) a rod guiding unit for guiding the longitudinally moving rod of material along its longitudinal axis, along an optical path within a transparent passageway, said optical path and said transparent passageway coaxially extend along said longitudinal axis of the moving rod of material; and
   (b) an electro-optical transmission module through which pass said optical path and said transparent passageway, said electro-optical transmission module includes:
      (i) an illumination unit for generating a focused beam of electromagnetic radiation, such that said focused beam is transmitted through a first side of said transparent passageway and incident upon the rod of material longitudinally moving within said transparent passageway, said incident focused beam illuminates a volumetric segment of the longitudinally moving rod of material, such that at least part of said incident focused beam is transmitted through said volumetric segment and through a second side of said transparent passageway, for forming a rod material volumetric segment transmitted beam; and
      (ii) a detection unit for detecting said rod material volumetric segment transmitted beam, for forming a detected rod material volumetric segment transmitted beam useable for determining the internal properties and characteristics of the longitudinally moving rod of material.

35. The device of claim 34, wherein said rod guiding unit includes a transparent housing, for housing, holding, or confining, said transparent passageway within which is said optical path, along which is guided the longitudinally moving rod of material.

36. The device of claim 35, wherein said transparent housing is of a hollow tubular or cylindrical geometrical shape, and is constructed from an optically transparent material.

37. The device of claim 34, wherein said illumination unit includes an electromagnetic radiation beam source, said electromagnetic radiation beam source is of structure and functions according to either light emitting diode technology, or fiber optic technology.

38. The device of claim 34, wherein said incident focused beam is of electromagnetic radiation selected from the group consisting of infrared radiation, visible light, and ultraviolet radiation.

39. The device of claim 34, wherein said incident focused beam is of infrared electromagnetic radiation having wavelength in a range of between about 900 nm and about 1000 nm.

40. The device of claim 34, wherein said incident focused beam is of infrared electromagnetic radiation having wavelength in a range of between about 920 nm and about 970 nm.

41. The device of claim 34, wherein said illumination unit includes components and is operated by a procedure for monitoring temperature and compensating for temperature changes in at least one critical region of operation of said illumination unit.

42. The device of claim 41, wherein said components of said illumination unit for said monitoring temperature and said compensating for said temperature changes include: a polarizing beam splitter, an optical feedback reference beam detector, an optical feedback reference beam signal amplifier, an illumination unit temperature sensor, an illumination unit temperature sensor signal amplifier, an illumination unit signal comparator, a proportional integrated regulator, a current regulator, and illumination unit electro-optical feedback loop component connections and linkages.

43. The device of claim 41, wherein a said critical region of operation is in immediate vicinity of said illuminated volumetric segment of the rod of material longitudinally moving along said optical path within said transparent passageway during the electro-optical inspection process.

44. The device of claim 41, wherein a said critical region of operation is in immediate vicinity where said incident focused beam is transmitted through said first side of said transparent passageway and incident upon said volumetric segment.

45. The device of claim 41, wherein said operation of said illumination unit including said components and said procedure for monitoring temperature and compensating for temperature changes is based on a temperature change monitoring and compensating electro-optical feedback loop.

46. The device of claim 34, wherein said detection unit includes at least one transmitted beam detector, each said transmitted beam detector is of structure and functions as a light receiving type of device selected from the group consisting of a phototransistor, a photosensitive transducer, a fiber optic conductor or guide, and a photoelectric element.

47. The device of claim 34, wherein said detection unit includes components and is operated by a procedure for monitoring temperature and compensating for temperature changes in at least one critical region of operation of said detection unit.

48. The device of claim 47, wherein said components of said detection unit for said monitoring temperature and said compensating for said temperature changes include: a detection unit temperature sensor, a detection unit temperature sensor signal amplifier, and a detection unit signal comparator.

49. The device of claim 47, wherein a said critical region of operation is in immediate vicinity of said illuminated volumetric segment of the rod of material longitudinally moving along said optical path within said transparent passageway.

50. The device of claim 47, wherein a said critical region of operation is in immediate vicinity where said rod material volumetric segment transmitted beam is transmitted from said volumetric segment and then transmitted through said second side of said transparent passageway, and then detected and received by said detection unit.

51. The device of claim 47, wherein said operation of said detection unit including said components and said procedure for monitoring temperature and compensating for temperature changes is based on a temperature change monitoring and compensating electro-optical detection circuit.

52. The device of claim 34, wherein the internal properties and characteristics are density, structure, defects, and impurities, and variabilities thereof, of the longitudinally moving rod of material.

53. The device of claim 34, wherein said electro-optical transmission module includes a module housing through which passes said transparent passageway within which is said guided longitudinally moving rod of material.

54. The device of claim 53, wherein said module housing includes components and is operated by a procedure for monitoring temperature and compensating for temperature changes in at least one critical region of operation of said module housing.

55. The device of claim 54, wherein said components of said module housing for said monitoring temperature and said compensating for said temperature changes include: a module housing temperature sensor, and associated electro-optical circuitry.

56. The device of claim 34, further including components for preventing, eliminating, or reducing, radially directed vibrating of the longitudinally moving rod of material during electro-optically inspecting the longitudinally moving rod of material.

57. The device of claim 56, wherein said components include: a vortex generating mechanism, for generating a continuous vortical type of flow of gas within and along said transparent passageway.

58. The device of claim 57, wherein pressure, and linear flow velocity, of said flow of gas are about one atmosphere above room atmospheric pressure, and about 100 meters per minute, respectively.

59. The device of claim 57, wherein operation of said vortex generating mechanism also cleans said rod guiding unit and cleans said transparent passageway during the electro-optical inspection process.

60. The device of claim 56, wherein said components include: a vortex generating mechanism, for generating a continuous vortical type of flow of gas within and along said transparent passageway, such that said flowing gas rotates as a vortex around said optical path and around the longitudinally moving rod of material, and flows downstream within and along said transparent passageway in same longitudinal direction of the longitudinally moving rod of material, such that said flowing gas radially impinges upon the longitudinally moving rod of material within said transparent passageway, whereby said flowing gas radially impinging upon the longitudinally moving rod of material prevents, eliminates, or reduces, radially directed vibrating of the longitudinally moving rod of material during the electro-optically inspecting the longitudinally moving rod of material.

61. The device of claim 34, further including components for cleaning said rod guiding unit and cleaning said transparent passageway during the electro-optical inspection process.

62. The device of claim 61, wherein said components include: a vortex generating mechanism, for generating a continuous vortical type of flow of gas within and along said transparent passageway, whereby said flow of gas cleans said rod guiding unit and cleans said transparent passageway during the electro-optical inspection process.

63. The device of claim 34, wherein the longitudinally moving rod of material is a longitudinally moving cigarette rod.

64. The device of claim 34, wherein the longitudinally moving rod of material is a longitudinally moving cigarette rod consisting of processed tobacco inside a rolled and sealed tube of cigarette wrapping paper.

65. The device of claim 34, wherein said optical path and said transparent passageway coaxially extend along said longitudinal axis of the moving rod of material and pass through a plurality of more than one said electro-optical transmission module.

66. The device of claim 65, wherein each of said plurality of said electro-optical transmission modules is positionable at a different longitudinal position or location around and along said transparent passageway within which extends said optical path.

67. The device of claim 65, wherein each of said plurality of said electro-optical transmission modules is positionable at a same or different angular, radial, or circumferential, position or location around said transparent passageway within which extends said optical path.

68. The device of claim 65, wherein longitudinal and angular or circumferential positions of said plurality of said electro-optical transmission modules, relative to each other, and relative to said transparent passageway within which extends said optical path, are spatially staggered or displaced along said optical path, along which the longitudinally moving rod of material is guided by said rod guiding unit.

69. The device of claim 65, wherein each said electro-optical transmission module through which pass said optical path and said transparent passageway includes a paired said illumination unit and said detection unit.

70. The device of claim 69, wherein said paired illumination and detection units of said plurality of said electro-optical transmission modules are temporally continuously or discontinuously activated according to a pre-determined timing or switching schedule or sequence, while the longitudinally moving rod of material is continuously or intermittently moving and being guided through said plurality of electro-optical transmission modules.

71. The device of claim 70, wherein said pre-determined timing or switching schedule or sequence is effected via applying a synchronous or asynchronous on/off switching schedule or sequence for operating said paired illumination and detection units.

72. A device for preventing, eliminating, or reducing, radially directed vibrating of a longitudinally moving rod of material during electro-optically inspecting the longitudinally moving rod of material, comprising: a rod guiding unit for guiding the longitudinally moving rod of material along its longitudinal axis, along an optical path within a transparent passageway, said optical path and said transparent passageway coaxially extend along said longitudinal axis of the longitudinally moving rod of material and pass through an electro-optical inspection apparatus used for electro-optically inspecting the longitudinally moving rod of material, said rod guiding unit includes a vortex generating mechanism for generating a continuous vortical type of flow of gas within and along said transparent passageway, such that said flowing gas rotates as a vortex around said optical path and around the longitudinally moving rod of material, and flows downstream within and along said transparent passageway in same longitudinal direction of the longitudinally moving rod of material, such that said flowing gas radially impinges upon the longitudinally moving rod of material within said transparent passageway, whereby said flowing gas impinging upon the longitudinally moving rod of material prevents, eliminates, or reduces, radially directed vibrating of the longitudinally moving rod of material, during the electro-optically inspecting the longitudinally moving rod of material.

73. The device of claim 72, wherein pressure, and linear flow velocity, of said flow of gas are about one atmosphere above room atmospheric pressure, and about 100 meters per minute, respectively.

* * * * *